US011655225B2

(12) United States Patent
Day et al.

(10) Patent No.: US 11,655,225 B2
(45) Date of Patent: May 23, 2023

(54) ANTIMYCOBACTERIAL HETEROCYCLIC AMIDES

(71) Applicant: Crestone, Inc., Boulder, CO (US)

(72) Inventors: Joshua Day, Boulder, CO (US); James Graham, Boulder, CO (US); Thale Jarvis, Boulder, CO (US); Elizabeth Mcfaddin, Nederland, CO (US); Urs Ochsner, Boulder, CO (US); Xicheng Sun, Boulder, CO (US); Christina Wong, Boulder, CO (US)

(73) Assignee: CRESTONE, INC., Boulder, CO (US)

( * ) Notice: Subject to any disclaimer, the term of this patent is extended or adjusted under 35 U.S.C. 154(b) by 123 days.

(21) Appl. No.: 16/976,743

(22) PCT Filed: Feb. 28, 2019

(86) PCT No.: PCT/US2019/020095
§ 371 (c)(1),
(2) Date: Aug. 28, 2020

(87) PCT Pub. No.: WO2019/169158
PCT Pub. Date: Jun. 9, 2019

(65) Prior Publication Data
US 2021/0002239 A1 Jan. 7, 2021

Related U.S. Application Data

(60) Provisional application No. 62/636,328, filed on Feb. 28, 2018.

(51) Int. Cl.
| | | |
|---|---|---|
| *C07D 277/82* | (2006.01) | |
| *C07D 235/30* | (2006.01) | |
| *C07D 263/58* | (2006.01) | |
| *C07D 277/68* | (2006.01) | |
| *C07D 333/72* | (2006.01) | |
| *A61P 31/04* | (2006.01) | |
| *A61P 31/06* | (2006.01) | |

(52) U.S. Cl.
CPC ............ *C07D 277/82* (2013.01); *A61P 31/04* (2018.01)

(58) Field of Classification Search
CPC .. C07D 277/82; C07D 235/30; C07D 263/58; C07D 277/68; C07D 333/72; A61P 31/04; A61P 31/06
See application file for complete search history.

(56) References Cited

U.S. PATENT DOCUMENTS

| | | | |
|---|---|---|---|
| 2005/0192275 A1 | 9/2005 | Arora et al. | |
| 2010/0179122 A1 | 7/2010 | Lindsley et al. | |
| 2015/0225388 A1 | 8/2015 | Willand et al. | |
| 2015/0246024 A1 | 9/2015 | Richter et al. | |
| 2017/0044100 A1 | 2/2017 | Bishai et al. | |

FOREIGN PATENT DOCUMENTS

| | | |
|---|---|---|
| JP | 2017-523966 | 8/2017 |
| JP | 2017-531674 | 10/2017 |
| WO | WO 2005/037845 A1 | 4/2005 |
| WO | WO 2006117306 A1 | 11/2006 |

OTHER PUBLICATIONS

PreventBacterialInfection, 2022, https://www.health.harvard.edu/staying-healthy/how-to-prevent-infections.*
RN 2105938-07-4, registry database compound, 2017.*
RN2175490-14-7, registry database compound, 2018.*
RN2177947-85-0, registry database compound, 2018.*
RN2178397-20-9, registry database compound, 2018.*
Extended European Search Report for PCT/US2019/020095, dated Jan. 21, 2022, 12 pages.
Graham et al. "Discovery of benzothiazole amides as potent antimycobacterial agents", Bioorg. Med. Chem. Lett., vol. 28, No. 19, Aug. 25, 2018, pp. 3177-3181.
International Search Report for PCT/US2019/020095, dated Jun. 7, 2019, 17 pages.
"High Throughput Screening for Inhibitors of *Mycobacterium tuberculosis* H37Rv," Ananthan, Subramaniam, et al., Tuberculosis (Edinburgh, Scotland), Sep. 2009, pp. 334-353.
Office Action dated May 6, 2021 with respect to India App. No. 202017036759 (w/ English Trans.), 5 pp.
Office Action dated Nov. 19, 2021 with respect to Japanese App. No. 2020-545340 (w/ English Trans.), 10 pp.
JPO; Office Action dated Jun. 28, 2022 with respect to Japanese App. No. 2020-545340 (wEnglish Translation), 5 pages.

* cited by examiner

*Primary Examiner* — Sun Jae Yoo
(74) *Attorney, Agent, or Firm* — Snell & Wilmer LLP

(57) ABSTRACT

The present invention provides novel heterocylic amide compounds having useful antimycobacterial activity. Use of these compounds as pharmaceutical compositions and method of their production are also provided.

8 Claims, 2 Drawing Sheets

Figure 1. Metabolic labeling with [$^{14}$C]acetate. A. Total lipids; B. Cell wall-bound mycolates
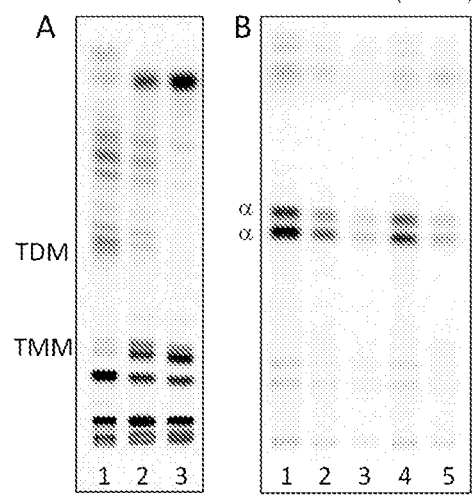

Figure 2. Efficacy (A) and Tolerability (B) of CRS400226, dosed intratracheally, in a mouse model of *Mabs* lung infection
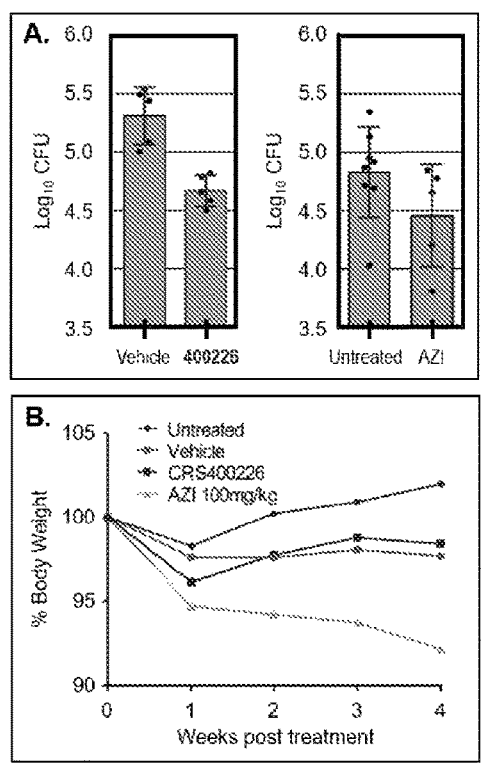

ANTIMYCOBACTERIAL HETEROCYCLIC AMIDES

TECHNICAL FIELD

The present disclosure relates to novel heterocyclic amide compounds useful in the treatment of infection caused by mycobacteria such as nontuberculosus and tuberculosis. The present disclosure further relates to methods for preparation of the novel compounds and to pharmaceutical compositions containing the novel compounds useful in the treatment of mycobacterial infection.

BACKGROUND OF THE INVENTION

Mycobacteria remain important, often drug-resistant human pathogens worldwide, including M. tuberculosis and the historically less-appreciated non-tuberculous mycobacteria (NTM). Pulmonary NTM disease is steadily increasing in the U.S., from 86,000 cases in 2010 to an estimated 181,000 cases in 2014, with associated direct medical costs of $1.7 billion (Strollo, S. E., et al. Ann Am Thorac Soc 12, 1458-1464, 2015). Underlying lung conditions that lead to increased susceptibility include bronchiectasis, chronic obstructive pulmonary disease, and cystic fibrosis (Marras, T. K., et al. Clin Chest Med 23, 553-567, 2002; De Groote, M. A., et al. Clin Infect Dis 42, 1756-1763. 2006; Adjemian, J., et al Am J Respir Crit Care Med 185, 881-886, 2012; Skolnik, K., et al. Curr Treat Options Infect Dis 8, 259-274, 2016; Cavalli, Z., et al. J Cyst Fibros 16, 579-584, 2017). Other risk factors are primary immunodeficiency involving IL-12, TNFα or IFN-γ pathway abnormalities (Lake, M. A., et al. BMC Med 14, 54, 2016), reduced immune competence due to HIV infection (Vinnard, C., et al. Ann Am Thorac Soc 13, 1951-1955, 2016), or immunosuppressive medications (Winthrop, K. L., et al. Ann Rheum Dis 72, 37-42, 2013). The epidemiology also reflects demographic risk factors such as age >60 years and female gender (Prevots, D. R., et al. Am J Respir Crit Care Med 182, 970-976, 2010; Lake, M. A., et al. BMC Med 14, 54, 2016). Tuberculosis (TB) remains an ongoing global public health threat, with over two billion people carrying the infection worldwide. M. tuberculosis (Mtb) bacilli can remain latent for extended periods of time; nonetheless, the large reservoir of latent infection fuels a growing population with active disease, amounting to an estimated 10.4 million new TB cases and 1.7 million deaths in 2016 (WHO, 2017). The vast majority of TB cases occur in 30 high-burden countries (WHO, 2017). In the U.S., a total of 9,287 new TB cases were reported for 2016 (Schmit, K. Tuberculosis—United States. Prevention Morbidity and Mortality Weekly Report 66, 289-294, 2017). From 1999-2014, TB-related mortality in the U.S. decreased by over 50%, down to 1,021 deaths in 2014, corresponding to a mortality rate of 3.3 TB-related deaths per 1,000,000 person-years (Vinnard, C., et al. Ann Am Thorac Soc 13, 1951-1955, 2016). In contrast, NTM-related deaths remained largely unchanged during this time period, with a mortality rate of 2.3 NTM-related deaths per 1,000,000 person-years. The prevalence of NTM infections has now surpassed TB in some countries (Low, J. L., et al. Front Microbiol 8, 1539, 2016). Of note, the epidemiology of fatal NTM infections is changing, with a decrease of cases in HIV-infected individuals and an increase in deaths in older white women (Vinnard, C., et al. Ann Am Thorac Soc 13, 1951-1955, 2016).

Mycobacterial pathogens are intrinsically resistant to many antibiotics and pose an enormous human health issue and a major threat to disease control worldwide (Fonseca, J. D., et al. Int J Infect Dis 32, 94-100, 2015). Antibiotic resistance mechanisms in M. tuberculosis are fairly well understood and include 1) intrinsic resistance through low permeability of the cell wall, acquired resistance through chromosomal mutations, specialized resistance mechanisms based on target alteration, 2) target mimicry, or direct effects on the drug via its modification, degradation, or efflux, and 3) phenotypic tolerance due to epigenetics in response to metabolic or physiological changes that can lead to persisters (Nguyen, L. (2016). Arch Toxicol 90, 1585-1604; Gold, B., et al Microbiol Spectr 5, 2017; Jansen, R. S., et al. Trends Pharmacol Sci 38, 393-405, 2017). Continued selective pressure has led to cumulative resistance to first-line and second-line drugs seen in multidrug-resistant (MDR), extensively drug-resistant (XDR), and eventually totally drug-resistant (TDR) M. tuberculosis strains (Dorman, S. E., et al. Nat Med 13, 295-298, 2007; Udwadia, Z. F. Thorax 67, 286-288, 2012). Infections with XDR M. tuberculosis strains put the global TB control programs at risk. XDR-TB cases do occur in the U.S. and are associated with estimated average cost of $483,000 per case, and XDR-TB mortality rates are reminiscent of those in the pre-antibiotic era (CDC, 2009).

Although therapeutic agents developed to treat Mtb infections often lack activity against NTM, it remains an attractive approach to initiate new NTM drug discovery projects via screening a library of TB active compounds against NTM, which has indeed resulted in high hit rates (Low, J. L., et al. Front Microbiol 8, 1539, 2016). Among older drugs, a potential role for clofazimine in NTM treatment regimens has been suggested, since this agent showed bactericidal activity and synergy with amikacin or clarithromycin, both of which are commonly used antibiotics to treat NTM infections (Ferro, B. E., et al. Antimicrob Agents Chemother, 60, 1097-1105, 2016). NTM treatment regimens differ by species, particularly between rapid growers (RGM) comprised of M. abscessus (Mabs) complex (M. abscessus, ssp. abscessus, bolletti, and massiliensis), M. chelonae, M. fortuitum, and others; and slow growers represented by M. avium, M. intracellurare, and M. chimaera (M. avium complex, or MAC). In general, drug treatment is long, costly, and often associated with drug-related toxicities and poor outcomes (van Ingen, J., et al. Drug Resist Updat 15, 149-161, 2012; Kasperbauer, S. H., et al. Semin Respir Crit Care Med 29, 569-576, 2015). Treatment options for NTM are severely limited, prompting this proposal for development of novel antimycobacterial agents. M. abscessus complex in particular is an emerging NTM infection for which effective therapy is often elusive, burdensome and costly (Ballarino, G. J., et al Respir Med 103, 1448-1455, 2009; Griffith, 2010; Griffith, D. E. (2007). Curr Opin Infect Dis 20, 198-203; Leber, A., et al. Eur Respir J 37, 1158-1165, 2011). Treatment of Mabs infection typically includes 1-2 parenteral agents such as amikacin, cefoxitin, imipenem or tigecycline, combined with an oral macrolide such as clarithromycin or azithromycin (Kasperbauer, S. H., et al. Clin Chest Med 36, 67-78, 2015). Unfortunately, a recent surveillance revealed that only 16% of Mabs strains were susceptible to clarithromycin, while 24% were resistant and 59% expressed erm-inducible macrolide resistance (Lee, M., et al. N Engl J Med 367, 1508-1518, 2012). It is thus not surprising that the overall clinical and microbiological cure rate of Mabs infection is only 41% (Diel, R., et al. Chest 152, 120-142, 2017).

Acquisition of NTM infections occurs through environmental sources (Falkinham, J. O. J Appl Microbiol 107, 356-367, 2009), although person-to-person transmission of Mabs ssp. massiliense has been described among cystic fibrosis patients (Bryant, J. M., et al. Science 354, 751-757, 2016). Epidemics of NTM have occurred in hospitals due to contaminated equipment or water supply lines (Aitken, M. L., et al Am J Respir Crit Care Med 185, 231-232, 2012; D'Antonio, S., et al. Int J Mycobacteriol 5, 244-247, 2016). One massive outbreak of skin and soft tissue infections in Brazil was caused by a laparoscope contaminated with a Mabs ssp. massiliense strain resistant to 2% glutaraldehyde that had been used for disinfection (Lorena, N. S., et al. Rev Col Bras Cir 36, 266-267, 2009; Duarte, R. S., et al. J Clin Microbiol 47, 2149-2155, 2010). Outbreaks of RGM infections unrelated to medical procedures have also been reported, including epidemics due to Mabs in recreational water (Dytoc, M. T., et al. Diagn Microbiol Infect Dis 53, 39-45, 2005), *M. gordonae* in drinking water (Lalande, V., et al. J Hosp Infect 48, 76-79, 2001), or tattoo ink contaminated with *M. chelonae* (Kennedy, B. S., et al. N Engl J Med 367, 1020-1024, 2012).

SUMMARY OF THE INVENTION

It has now been found that substituted heterocyclic amide compounds are useful in the treatment of mycobacterial infections. The present invention relates to these antimycobacterial compounds and salts thereof, pharmaceutical compositions comprising these compounds and methods of use thereof in the treatment of mycobacterial infections, including resistant mycobacterial infections.

In one aspect the invention provides compounds of Formula (I):

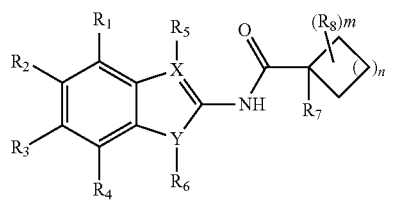

Formula I in which:
X is selected from C or N,
Y is selected from N, O or S,
n=1-6
R1, R2, R3, R4 are independently selected from the group consisting of H, halogens, small alkyl (C1-C6), small alkyloxy (C1-C6), halogenated small alkyl (C1-C6), halogenated small alkyloxy (C1-C6), carboxylates and further,
when X is carbon, R5 is selected from the group consisting of H, alkyl, halogens, and cyano; when X is N, R5 is null,
when Y is nitrogen, R6 is selected from the group consisting of H, alkyl, and substituted alkyl; when Y is 0 or S, R6 is null,
R7 is selected from the group consisting of H, small alkyl (C1-C6), halogenated small alkyl (C1-C6), R7 can not be H when n<3, each R8 is independently selected from the group consisting of H, small alkyl (C1-C6), halogenated small alkyl (C1-C6), m is 1-6,
R7 and R8 can link together to form rings when they are alkyl or halogenated alkyl.

These and various other features as well as advantages which characterize the invention will be apparent from a reading of the following detailed description and a review of the appended claims.

BRIEF DESCRIPTION OF THE DRAWING FIGURES

FIGS. 1A and 1B show metabolic labeling with $[C^{14}]$ acetate; and

FIGS. 2A and 2B show efficacy (A) and tolerability (B) of CRS400226, dosed intratracheally, in a mouse model of Mabs lung infection.

DETAILED DESCRIPTION OF THE INVENTION

The present invention relates to antimycobacterial compounds and salts thereof, pharmaceutical compositions comprising these compounds and methods of use thereof. The compounds of the present invention are useful in the protection of patients from bacterial infections, including antibiotic resistant bacterial infections.

In particular, antimycobacterial compounds of the invention include heterocyclic amide compounds.

In one embodiment, the invention provides compounds of Formula (I):

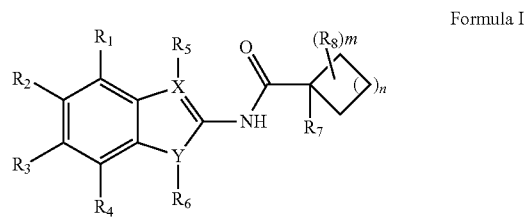

Formula I

In one embodiment,
X is selected from C or N,
Y is selected from N, O or S,
n=1-6,
R1, R2, R3, R4 are independently selected from the group consisting of H, halogens, small alkyl (C1-C6), small alkyloxy (C1-C6), halogenated small alkyl (C1-C6), halogenated small alkyloxy (C1-C6), and carboxylates, when X is carbon, R5 is selected from the group consisting of H, alkyl, halogens, and cyano; when X is nitrogen, R5 is null, when Y is nitrogen, R6 is selected from the group consisting of H, alkyl, and substituted alkyl; when Y is 0 or S, R6 is null,
R7 is selected from the group consisting of H, small alkyl (C1-C6), halogenated small alkyl (C1-C6), R7 can not be H when n<3, each R8 is independently selected from the group consisting of H, small alkyl (C1-C6), halogenated small alkyl (C1-C6), m is 1-6,
R7 and R8 can link together to form rings when they are alkyl or halogenated alkyl with proviso that

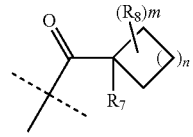

does not include:
4-propylcyclohexane-1-carbonyl, 1,2,2,3,3,4,4,5,5,6,6-undecafluorocyclohexane-1-carbonyl, 4-methylcyclohexane-1-carbonyl, 4-butylcyclohexane-1-carbonyl, cyclohexanecarbonyl, cyclopentanecarbonyl, cyclobutanecarbonyl, cycloheptanecarbonyl, 3-(trifluoromethyl)cyclohexane-1-carbonyl, 4,4-difluorocyclohexane-1-carbonyl, bicyclo[3.1.0]hexane-3-carbonyl, 1-methylcyclopentane-1-carbonyl, bicyclo[2.2.1]heptane-2-carbonyl, adamantane-1-carbonyl, 3-bromoadamantane-1-carbonyl, 3-chloroadamantane-1-carbonyl, 3,5-dimethyladamantane-1-carbonyl, 3-methyladamantane-1-carbonyl, 5,5,6-trifluoro-6-(trifluoromethyl)bicyclo[2.2.1]heptane-2-carbonyl, adamantane-2-carbonyl.

1-isobutylcyclopentane-1-carbonyl, pivalyl, 2-methyl-7-oxabicyclo[2.2.1]heptane-2-carbonyl, 5-methylbicyclo[3.3.1]nonane-1-carbonyl, 3-methylbicyclo[3.1.0]hexane-3-carbonyl, 1-ethylcyclohexane-1-carbonyl 1-methylcyclohexane-1-carbonyl, bicyclo[3.3.1]nonane-3-carbonyl, cyclohexanecarbonyl cyclooctanecarbonyl, 3,3,5-trimethyl-cyclohexane-1-carbonyl.

When used herein, the term "alkyl" and similar terms such as "alkoxy" include all straight chain, branched, and cyclic isomers. Alkyl refers to a saturated branched, straight-chain or cyclic monovalent hydrocarbon radical having the stated number of carbon atoms (i.e., C1-C6 means one to six carbon atoms) that is derived by the removal of one, two, or three hydrogen atoms from a parent alkane. Representative examples thereof include methyl, ethyl, n-propyl, iso-propyl, cyclobutyl, cyclopropyl, cyclopentyl, cyclohexyl, n-butyl, sec-butyl, iso-butyl, t-butyl, n-pentyl, n-hexyl, methylene, and Suitable identities for

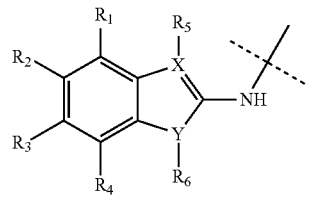

include, but are not limited to: 5-trifluoromethyl-benzo[d]thiazol-2-amine; 6-isopropyl-benzo[d]thiazol-2-amine; 6-butyl-benzo[d]thiazol-2-amine, 6-dimethylamino-benzo[d]thiazol-2-amine, [1,3]dioxolo[4',5':4,5]benzo[1,2-d]thiazol-6-amine, 6-ethoxybenzo[d]thiazol-2-amine, 6-isopropoxybenzo[d]thiazol-2-amine, 5,7-difluorobenzo[d]thiazol-2-amine, 5,7-dichlorobenzo[d]thiazol-2-amine, 5,7-dimethylbenzo[d]thiazol-2-amine, 6-(methylthio)benzo[d]thiazol-2-amine, 6-(difluoromethoxy)benzo[d]thiazol-2-amine, 6-(trifluoromethoxy)benzo[d]thiazol-2-amine, 6-(tert-butyl)benzo[d]thiazol-2-amine, 7-fluorobenzo[d]thiazol-2-amine, 6-bromo-4-fluoro-benzo[d]thiazol-2-amine, 5-bromo-benzo[d]thiazol-2-amine, 5-chloro-benzo[d]thiazol-2-amine, ethyl 2-aminobenzo[d]thiazole-6-carboxylate, 6-bromo-benzo[d]thiazol-2-amine, 5-fluoro-benzo[d]thiazol-2-amine, 4-fluoro-benzo[d]thiazol-2-amine, 5,6-difluoro-benzo[d]thiazol-2-amine, 4,5,6-trifluoro-benzo[d]thiazol-2-amine, 4,6-dichloro-benzo[d]thiazol-2-amine, 6-methyl-benzo[d]thiazol-2-amine, 6-fluoro-benzo[d]thiazol-2-amine, benzo[d]thiazol-2-amine, 4-fluoro-benzo[d]thiazol-2-amine, 6-chloro-benzo[d]thiazol-2-amine, 6-methoxy-benzo[d]thiazol-2-amine, 6-trifluoromethyl-benzo[d]thiazol-2-amine, 4,6-difluoro-benzo[d]thiazol-2-amine, 4-trifluoromethyl-benzo[d]thiazol-2-amine, 6-trifluoromethyl-benzo[d]thiazol-2-amine.

Suitable identities for

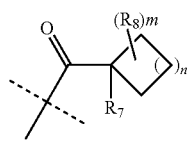

include, but are not limited to: (1R,2R,4R)-2-methylbicyclo[2.2.1]hept-5-ene-2-carbonyl, (1R,2S,4R)-2-methylbicyclo[2.2.1]hept-5-ene-2-carbonyl, decahydronaphthalene-2-carbonyl, (1R,3S)-1,2,2,3-tetramethylcyclopentane-1-carbonyl, 3,3-difluoro-1-methylcyclopentane-1-carbonyl, 3,3-dimethylcyclopentane-1-carbonyl, 1-ethylcyclopentane-1-carbonyl, 3-methylcyclopentane-1-carbonyl, cyclopentanecarbonyl, 1-methylcycloheptane-1-carbonyl, 1,2-dimethyl-cyclopentane-1-carbonyl, 2-methylbicyclo[2.2.1]heptane-2-carbonyl, 1,3-dimethylcyclopentane-1-carbonyl,

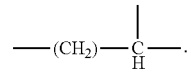

Optionally fluorosubstituted alkyls may have 1 or more substitutions of F for H on the alkyl chain. A representative example of an optionally fluorosubstituted alkyl is trifluoromethyl.

When used herein, the terms "alkenyl" and "alkynyl" include all straight chain, branched and cyclic isomers. Representative examples thereof include vinyl, ethynyl and 1-propynyl. Optionally fluorosubstituted alkenyls may have 1 or more substitutions of F for H on the alkenyl chain. A representative example of an optionally fluorosubstituted alkenyl is fluorovinyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino (e.g., pyridyloxy), ureido, $(C_{1-6})$alkoxycarbonylamino, 2,2,2-trichloroethoxycarbonylamino, aryl, heteroaryl, heterocyclyl, hydroxy, $(C_{1-6})$alkoxy (e.g., ethoxy, isopropoxy), acyloxy (e.g., phenyloxy, benzyloxy, phenethoxy), oxo, acyl, 2-thienoyl, $(C_{1-6})$alkylthio, $(C_{1-6})$alkylsulphinyl, $(C_{1-6})$alkylsulphonyl, hydroxyimino, $(C_{1-6})$alkoxyimino, hydrazino, hydrazono, benzohydroximoyl, guanidino, amidino and iminoalkylamino. Also preferred are 4-formyl-piperazin-1-yl, 4-methylpiperazin-1-yl-, 4-ethylpiperazin-1-yl-, 4-phenylpiperazin-1-yl-, 4-pyrimidin-2-yl-piperazin-1-yl, Hexahydroxy-pyrrolo[1,2-a]imidazole-1-yl, Morpholin-4-yl, 3-(2-methoxy-ethyl)-methyl-amino, and 3-(2-methoxy-ethyl)-methyl-amino. Other appropriate substituents include alkylthio meaning an alkyl-S— group in which the alkyl group is as previously described. Non-limiting examples of suitable alkylthio groups include methylthio and ethylthio. The bond to the parent moiety is through the sulfur. Substituents further include alkoxycarbonyl meaning an alkyl-O—CO— group. Non-limiting examples of suitable alkoxycarbonyl groups include methoxycarbonyl and ethoxycarbonyl. The bond to the parent moiety is through the carbonyl. Another suitable substituent is alkylsulfonyl meaning an alkyl-$SO_2$ group. Preferred alkylsulfonyl groups are those in which the alkyl group is a lower alkyl. The bond to the parent moiety is through the sulfonyl.

When used herein, the term "aryl" means an aromatic monocyclic or multicyclic ring system with each ring comprising from about 6 to about 14 carbon atoms, preferably about 6 to about 10 carbon atoms. The aryl group can be optionally substituted with one or more "ring system substituents" and optionally substituted with up to five, preferably up to three substituents which may be the same or different, and are as defined herein. Non-limiting examples of suitable aryl groups include phenyl, naphthyl, anthracenyl, phenanthrenyl, indanyl, indenyl, and the like. Aryl moieties are well known and described, for example, in Hawley's Condensed Chemical Dictionary (13 ed.), R. J. Lewis, ed., J. Wiley & Sons, Inc., New York (1997). Aryl groups can be substituted or unsubstituted.

When substituted, an aryl group may have up to three substituents. Preferred substituents for an aryl group (a "ring system substituent") include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, aryl$C_{(1-6)}$alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$ alkylcarbamoyl, heteroaryl and heterocyclyl. Other preferred aryl groups include arylalkyl meaning an alkyl substituted aryl group. Other preferred aryl groups include aryloxy meaning an aryl-O— group in which the aryl group is as previously described. Non-limiting examples of suitable aryloxy groups include phenoxy and naphthoxy. The bond to the parent moiety is through the ether oxygen. Arylalkyloxy meaning an arylalkyl-O— group in which the arylalkyl group is as previously described. Non-limiting examples of suitable arylalkyloxy groups include benzyloxy and phenethyloxy. The bond to the parent moiety is through the ether oxygen. Another preferred aryl is an arylthio meaning an aryl-S— group in which the aryl group is as previously described. Non-limiting examples of suitable arylthio groups include phenylthio and naphthylthio. The bond to the parent moiety is through the sulfur. Other preferred aryls include arylalkylthio meaning an arylalkyl-S— group in which the arylalkyl group is as previously described. Non-limiting example of a suitable arylalkylthio group is benzylthio. The bond to the parent moiety is through the sulfur. Other preferred aryls is an aryloxycarbonyl meaning an aryl-O—C(O)— group. Non-limiting examples of suitable aryloxycarbonyl groups include phenoxycarbonyl and naphthoxycarbonyl. The bond to the parent moiety is through the carbonyl. Another such group is an arylalkoxycarbonyl meaning an arylalkyl-O—C(O)— group. Non-limiting example of a suitable arylkoxycarbonyl group is benzyloxycarbonyl. The bond to the parent moiety is through the carbonyl. Yet another such group is an arylsulfonyl meaning an aryl-SO$_2$— group. The bond to the parent moiety is through the sulfonyl.

When used herein, the term "heteroaryl" monocyclic and polycyclic aromatic hydrocarbons include at least one heteroatom ring member such as sulfur, oxygen, or nitrogen alone or in combination. Preferably the heteroaryl ring comprises from 4 to 7, and preferably 5 to 6, ring atoms. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. Heteroaryl groups can be substituted or unsubstituted. A fused heteroaryl ring system may include carbocyclic rings and need only include one heterocyclic ring.

When used herein, the term "heterocyclyl" means an aromatic or non-aromatic saturated monocyclic or multicyclic (preferably bicyclic) ring system comprising about 3 to about 10 ring atoms, preferably about 5 to about 10 ring atoms, in which one or more of the atoms in the ring system is an element other than carbon, for example nitrogen, oxygen or sulfur, alone or in combination. Suitably the heterocyclic ring comprises from 4 to 7, preferably 5 to 6, ring atoms. A fused heterocyclic ring system may include carbocyclic rings and need only include one heterocyclic ring. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, pyrimidyl, oxazolidinyl, and the like.

When substituted, a heteroaryl or a heterocyclyl group may have up to three substituents. Preferred such substituents include those previously mentioned for an aryl group as well as oxo.

When used herein, the terms "halogen" and "halo" refer to fluoro, chloro, bromo and iodo.

When used herein, the term "acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

When used herein, the term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences. When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, N.Y.

When any variable (e.g., aryl, heterocycle, R2, etc.) occurs more than one time in any constituent or in Formula (I), its definition on each occurrence is independent of its definition at every other occurrence.

When used herein, the term "composition" is intended to encompass a product comprising the specified ingredients in the specified amounts, as well as any product which results, directly or indirectly, from combination of the specified ingredients in the specified amounts.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

It will be appreciated that certain compounds of the present invention may comprise one or more chiral centers so that compounds may exist as stereoisomers, including diastereoisomers and enantiomers. The present invention covers all such stereoisomers, and mixtures thereof, including racemates.

Accordingly, the disclosure provides the following compounds:

N-(1-benzothiophen-2-yl)-5-methylbicyclo[3.3.1]nonane-1-carboxamide, N-(5,7-dichloro-1,3-benzothiazol-2-yl)-5-methylbicyclo[3.3.1]nonane-1-carboxamide, N-(5-bromo-1,3-benzothiazol-2-yl)-5-methylbicyclo[3.3.1]nonane-1-carboxamide, N-(5,7-difluoro-1,3-benzothiazol-2-yl)-5-methylbicyclo[3.3.1]nonane-1-carboxamide, 5-methyl-N-[6-(trifluoromethoxy)-1,3-benzothiazol-2-yl]bicyclo[3.3.1]nonane-1-carboxamide, 1-methyl-N-[6-(trifluoromethoxy)-1,3-benzothiazol-2-yl]cycloheptane-1-carboxamide, N-[6-(trifluoromethoxy)-1,3-benzothiazol-2-yl]adamantane-2-carboxamide, N-(5,7-dimethyl-1,3-benzothiazol-2-yl)-5-methylbicyclo[3.3.1]nonane-1-carboxamide, 5-methyl-N-(4,5,6-trifluoro-1,3-benzothiazol-2-yl)bicyclo[3.3.1]nonane-1-carboxamide, N-(4,6-difluoro-1,3-benzothiazol-2-yl)-5-methylbicyclo[3.3.1]nonane-1-carboxamide, N-(6-bromo-1,3-benzothiazol-2-yl)-5-methylbicyclo[3.3.1]nonane-1-carboxamide, N-(6-chloro-1,3-benzothiazol-2-yl)-5-methylbicyclo[3.3.1]nonane-1-carboxamide, N-[6-(difluoromethoxy)-1,3-benzothiazol-2-yl]-5-methylbicyclo[3.3.1]nonane-1-carboxamide, (3R,5S,7s)-N-[6-(trifluoromethoxy)-1,3-benzothiazol-2-yl]adamantane-1-carboxamide, N-[6-(trifluoromethoxy)-1,3-benzothiazol-2-yl]bicyclo[3.3.1]nonane-3-carboxamide, N-[6-(trifluoromethoxy)-1,3-benzothiazol-2-yl]-decahydronaphthalene-2-carboxamide, (1R,3S)-1,2,2,3-tetramethyl-N-[6-(trifluoromethoxy)-1,3-benzothiazol-2-yl]cyclopentane-1-carboxamide, N-(5,7-dichloro-1,3-benzothiazol-2-yl)-1-methylcycloheptane-1-carboxamide, N-(1-benzothiophen-2-yl)adamantane-2-carboxamide, N-(5,7-dichloro-1,3-benzothiazol-2-yl)adamantane-2-carboxamide, 5-methyl-N-[6-(trifluoromethyl)-1,3-benzothiazol-2-yl]bicyclo[3.3.1]nonane-1-carboxamide, 1,3-dimethyl-N-[6-(trifluoromethoxy)-1,3-benzothiazol-2-yl]cyclopentane-1-carboxamide, N-(5,7-dichloro-1,3-benzothiazol-2-yl)-1-methylcyclohexane-1-carboxamide, N-(5-bromo-1-benzothiophen-2-yl)-3,5-dimethyladamantane-1-carboxamide, 3,3,5-trimethyl-N-[5-(trifluoromethyl)-1,3-benzothiazol-2-yl]cyclohexane-1-carboxamide, N-(1-benzothiophen-2-yl)adamantane-1-carboxamide, 1-ethyl-N-[6-(trifluoromethoxy)-1,3-benzothiazol-2-yl]cyclohexane-1-carboxamide, 1-methyl-N-[6-(trifluoromethoxy)-1,3-benzothiazol-2-yl]cyclohexane-1-carboxamide, N-[6-(trifluoromethoxy)-1,3-benzothiazol-2-yl]tricyclo[3.3.1.0$^{3,7}$]nonane-3-carboxamide, (3R,5S,7s)-N-(4,5,6-trifluoro-1,3-benzothiazol-2-yl)adamantane-1-carboxamide, N-(5,7-difluoro-1,3-benzothiazol-2-yl)-3,5-dimethyladamantane-1-carboxamide, N-(5,7-difluoro-1,3-benzothiazol-2-yl)-3,3,5-trimethylcyclohexane-1-carboxamide, N-(4,6-difluoro-1,3-benzothiazol-2-yl)bicyclo[3.3.1]nonane-3-carboxamide, N-(5,7-dichloro-1,3-benzothiazol-2-yl)-3,5-dimethyladamantane-1-carboxamide, N-(5,7-dichloro-1,3-benzothiazol-2-yl)-3,3,5-trimethylcyclohexane-1-carboxamide, N-[6-(trifluoromethoxy)-1,3-benzothiazol-2-yl]cyclooctanecarboxamide, N-(5-chloro-1,3-benzothiazol-2-yl)-3,5-dimethyladamantane-1-carboxamide, N-(6-chloro-1,3-benzothiazol-2-yl)-3,5-dimethyladamantane-1-carboxamide, (1R,3R,7r)-3,5-dimethyl-N-[6-(trifluoromethyl)-1,3-benzothiazol-2-yl]adamantane-1-carboxamide, N-(1-benzothiophen-2-yl)bicyclo[3.3.1]nonane-3-carboxamide, N-(4,5,6-trifluoro-1,3-benzothiazol-2-yl)bicyclo[3.3.1]nonane-3-carboxamide, N-(1-benzothiophen-2-yl)-3,5-dimethyladamantane-1-carboxamide, N-(7-fluoro-1,3-benzothiazol-2-yl)-3,5-dimethyladamantane-1-carboxamide, N-(5,6-difluoro-1,3-benzothiazol-2-yl)-3,5-dimethyladamantane-1-carboxamide, 3,5-dimethyl-N-[6-(trifluoromethoxy)-1,3-benzothiazol-2-yl]adamantane-1-carboxamide, 3,3,5-trimethyl-N-[6-(trifluoromethoxy)-1,3-benzothiazol-2-yl]cyclohexane-1-carboxamide, N-(1-benzothiophen-2-yl)-3,3,5-trimethylcyclohexane-1-carboxamide, N-(5-bromo-1,3-benzothiazol-2-yl)-3,5-dimethyladamantane-1-carboxamide, N-(5,7-dichloro-1,3-benzothiazol-2-yl)-1-methylcyclopentane-1-carboxamide, (1R,2R,4R)-2-methyl-N-[6-(trifluoromethoxy)-1,3-benzothiazol-2-yl]bicyclo[2.2.1]hept-5-ene-2-carboxamide, 3,3-dimethyl-N-[6-(trifluoromethoxy)-1,3-benzothiazol-2-yl]cyclopentane-1-carboxamide, 1-methyl-N-[6-(trifluoromethyl)-1,3-benzothiazol-2-yl]cycloheptane-1-carboxamide, N-(5-bromo-1,3-benzothiazol-2-yl)-1-methylcycloheptane-1-carboxamide, N-(1-benzothiophen-2-yl)-1-methylcycloheptane-1-carboxamide, N-(6-bromo-1,3-benzothiazol-2-yl)adamantane-2-carboxamide, N-(6-chloro-1,3-benzothiazol-2-yl)adamantane-2-carboxamide, N-(5,7-difluoro-1,3-benzothiazol-2-yl)adamantane-2-carboxamide, N-(4,5,6-trifluoro-1,3-benzothiazol-2-yl)adamantane-2-carboxamide, N-[6-(difluoromethoxy)-1,3-benzothiazol-2-yl]adamantane-2-carboxamide, 1,2-dimethyl-N-[6-(trifluoromethoxy)-1,3-benzothiazol-2-yl]cyclopentane-1-carboxamide, 3,5-dimethyl-N-[5-(trifluoromethyl)-1,3-benzothiazol-2-yl]adamantane-1-carboxamide, N-(6-bromo-1,3-benzothiazol-2-yl)bicyclo[3.3.1]nonane-3-carboxamide, N-[6-(difluoromethoxy)-1,3- benzothiazol-2-yl]bicyclo[3.3.1]nonane-3-carboxamide, N-(6-chloro-1,3-benzothiazol-2-yl)bicyclo[3.3.1]nonane-3-carboxamide, N-(5,7-dimethyl-1,3-benzothiazol-2-yl)-3,3,5-trimethylcyclohexane-1-carboxamide, N-(5,7-dichloro-1,3-benzoxazol-2-yl)-3,5-dimethyladamantane-1-carboxamide, 3,5-dimethyl-N-{6-[(trifluoromethyl)sulfanyl]-1,3-benzothiazol-2-yl}adamantane-1-carboxamide, N-[6-(difluoromethoxy)-1,3-benzothiazol-2-yl]-3,5-dimethyladamantane-1-carboxamide, N-(6-bromo-4-fluoro-1,3-benzothiazol-2-yl)-3,5-dimethyladamantane-1-carboxamide, N-(5-fluoro-1,3-benzothiazol-2-yl)-3,5-dimethyladamantane-1-carboxamide, N-(4,6-difluoro-1,3-benzothiazol-2-yl)-3,5-dimethyladamantane-1-carboxamide, N-(7-fluoro-1,3-benzothiazol-2-yl)-3,3,5-trimethylcyclohexane-1-carboxamide, N-(6-bromo-1,3-benzothiazol-2-yl)-3,5-dimethyladamantane-1-carboxamide, N-(6-fluoro-1,3-benzothiazol-2-yl)-3,3,5-trimethylcyclohexane-1-carboxamide, N-(6-chloro-1,3-benzothiazol-2-yl)-3,3,5-trimethylcyclohexane-1-carboxamide, N-(6-bromo-1,3-benzothiazol-2-yl)-3,3,5-trimethylcyclohexane-1-carboxamide, 3,3,5-trimethyl-N-(4,5,6-trifluoro-1,3-benzothiazol-2-yl)cyclohexane-1-carboxamide, 3,5-dimethyl-N-[6-(trifluoromethyl)-1,3-benzothiazol-2-yl]adamantane-1-carboxamide, 3,3,5-trimethyl-N-[6-(trifluoromethyl)-1,3-benzothiazol-2-yl]cyclohexane-1-carboxamide, N-(4,6-difluoro-1,3-benzothiazol-2-yl)-3,3,5-trimethylcyclohexane-1-carboxamide, 3,3-difluoro-1-methyl-N-[6-(trifluoromethoxy)-1,3-benzothiazol-2-yl]cyclopentane-1-carboxamide, N-(4,6-difluoro-1,3-benzothiazol-2-yl)adamantane-2-carboxamide, N-(5,7-dimethyl-1,3-benzothiazol-2-yl)adamantane-2-carboxamide, 1-methyl-N-[6-(trifluoromethyl)-1,3-benzothiazol-2-yl]cyclohexane-1-carboxamide, 1-(2-methylpropyl)-N-[6-(trifluoromethoxy)-1,3-benzothiazol-2-yl]cyclopentane-1-carboxamide, N-(4,6-difluoro-1,3-benzothiazol-2-yl)adamantane-1-carboxamide, N-[6-(difluoromethoxy)-1,3-benzothiazol-2-yl]adamantane-1-carboxamide, N-(5,6-difluoro-1,3-benzoxazol-2-yl)-3,5-dimethyladamantane-1-carboxamide, N-(1-benzothiophen-2-yl)cyclooctanecarboxamide, N-(5,7-dimethyl-1,3-benzothiazol-2-yl)-3,5-dimethyladamantane-1-carboxamide, N-[6-(difluoromethoxy)-1,3-benzothiazol-2-yl]-3,3,5-trimethylcyclohexane-1-carboxamide, N-(6-bromo-4-fluoro-1,3-benzothiazol-2-yl)-3,3,5-trimethylcyclohexane-1-carboxamide, N-(5-fluoro-1,3-benzothiazol-2-yl)-3,3,5-trimethylcyclohexane-1-carboxamide, N-(1,3-benzothiazol-2-yl)-3,5-dimethyladamantane-1-carboxamide, N-(4-chloro-1,3-benzothiazol-2-yl)-3,5-dimethyladamantane-1-carboxamide, N-(6-methoxy-1,3-benzothiazol-2-yl)-3,3,5-trimethylcyclohexane-1-carboxamide, N-(4,6-dichloro-1,3-benzothiazol-2-yl)-3,5-dimethyladamantane-1-carboxamide, 3,5-dimethyl-N-(6-methyl-1,3-benzothiazol-2-yl)adamantane-1-carboxamide, 3,5-dimethyl-N-[6-(trifluoromethyl)-1,3-benzothiazol-2-yl]cyclohexane-1-carboxamide, ethyl 2-(3,5-dimethyladamantane-1-amido)-1,3-benzothiazole-6-carboxylate, 1-ethyl-N-[6-(trifluoromethoxy)-1,3-benzothiazol-2-yl]cyclopentane-1-carboxamide, 3-methyl-N-[6-(trifluoromethoxy)-1,3-benzothiazol-2-yl]cyclopentane-1-carboxamide, 1-methyl-N-(4,5,6-trifluoro-1,3-benzothiazol-2-yl)cycloheptane-1-carboxamide, 2-methyl-N-[6-(trifluoromethoxy)-1,3-benzothiazol-2-yl]bicyclo[2.2.1]heptane-2-carboxamide, N-(1-benzothiophen-2-yl)-1-methylcyclohexane-1-carboxamide, N-(6-bromo-5,7-dimethyl-1,3-benzothiazol-2-yl)-1-methylcyclohexane-1-carboxamide, N-(6-chloro-1,3-benzothiazol-2-yl)adamantane-1-carboxamide, N-[6-(difluoromethoxy)-1,3-benzothiazol-2-yl]cyclooctanecarboxamide, N-(4,6-difluoro-1,3-benzothiazol-2-yl)cyclooctanecarboxamide, N-(6-chloro-1,3-benzothiazol-2-yl)cyclooctanecarboxamide, N-(6-ethoxy-1,3-benzothiazol-2-yl)-3,5-dimethyladamantane-1-carboxamide, N-(5,6-dichloro-1,3-benzoxazol-2-yl)-3,5-dimethyladamantane-1-carboxamide, N-(5,6-dichloro-1,3-benzoxazol-2-yl)-3,3,5-trimethylcyclohexane-1-carboxamide, N-(5-chloro-1,3-benzoxazol-2-yl)-3,3,5-trimethylcyclohexane-1-carboxamide, N-(6-bromo-1,3-benzoxazol-2-yl)-3,5-dimethyladamantane-1-carboxamide, N-(4,5,6-trifluoro-1,3-benzothiazol-2-yl)cyclooctanecarboxamide, N-(6-chloro-1,3-benzoxazol-2-yl)-3,5-dimethyladamantane-1-carboxamide, N-(6-chloro-1,3-benzoxazol-2-yl)-3,3,5-trimethylcyclohexane-1-carboxamide, N-(5,6-difluoro-1H-1,3-benzodiazol-2-yl)-3,5-dimethyladamantane-1-carboxamide, N-(6-fluoro-1H-1,3-benzodiazol-2-yl)-3,5-dimethyladamantane-1-carboxamide, N-(4-fluoro-1,3-benzothiazol-2-yl)-3,3,5-trimethylcyclohexane-1-carboxamide, N-(4-fluoro-1,3-benzothiazol-2-yl)-3,5-dimethyladamantane-1-carboxamide, N-(6-fluoro-1,3-benzothiazol-2-yl)-3,5-dimethyladamantane-1-carboxamide, N-(6-methoxy-1,3-benzothiazol-2-yl)-3,5-dimethyladamantane-1-carboxamide, N-(1,3-benzothiazol-2-yl)-3,3,5-trimethylcyclohexane-1-carboxamide, 3-(trifluoromethyl)-N-[6-(trifluoromethyl)-1,3-benzothiazol-2-yl]cyclohexane-1-carboxamide, 3-methyl-N-[6-(trifluoromethyl)-1,3-benzothiazol-2-yl]cyclohexane-1-carboxamide, 1-methyl-N-[6-(trifluoromethyl)-1,3-benzothiazol-2-yl]cyclopentane-1-carboxamide, (1R,2S,4R)-2-methyl-N-[6-(trifluoromethoxy)-1,3-benzothiazol-2-yl]bicyclo[2.2.1]hept-5-ene-2-carboxamide, N-[6-(trifluoromethoxy)-1,3-benzothiazol-2-yl]cyclopentanecarboxamide, N-(1,3-benzoxazol-2-yl)adamantane-2-carboxamide, 5-methyl-N-[6-(trifluoromethyl)-1,3-benzoxazol-2-yl]bicyclo[3.3.1]nonane-1-carboxamide, N-(5,7-difluoro-1,3-benzothiazol-2-yl)-1-methylcyclohexane-1-carboxamide, N-(6-bromo-1,3-benzothiazol-2-yl)-1-methylcyclohexane-1-carboxamide, N-(6-chloro-1,3-benzothiazol-2-yl)-1-methylcyclohexane-1-carboxamide, 1-methyl-N-[6-(trifluoromethoxy)-1,3-benzothiazol-2-yl]cyclopentane-1-carboxamide, 3-methyl-N-[6-(trifluoromethoxy)-1,3-benzothiazol-2-yl]bicyclo[3.1.0]hexane-3-carboxamide, N-(6-ethoxy-1,3-benzothiazol-2-yl)bicyclo[3.3.1]nonane-3-carboxamide, N-(4,6-difluoro-1,3-benzothiazol-2-yl)cycloheptanecarboxamide, N-(5-chloro-1,3-benzoxazol-2-yl)-3,5-dimethyladamantane-1-carboxamide, N-(4,5,6-trifluoro-1,3-benzothiazol-2-yl)cycloheptanecarboxamide, N-(5,7-dichloro-1,3-benzoxazol-2-yl)-3,3,5-trimethylcyclohexane-1-carboxamide, N-(5,7-dimethyl-1,3-benzoxazol-2-yl)-3,3,5-trimethylcyclohexane-1-carboxamide, N-(4-fluoro-1,3-benzoxazol-2-yl)-3,5-dimethyladamantane-1-carboxamide, N-(6-methoxy-1,3-benzoxazol-2-yl)-3,5-dimethyladamantane-1-carboxamide, N-(1H-1,3-benzodiazol-2-yl)-3,5-dimethyladamantane-1-carboxamide, N-(1,3-benzoxazol-2-yl)-3,5-dimethyladamantane-1-carboxamide, N-[6-(trifluoromethyl)-1,3-benzothiazol-2-yl]spiro[2.5]octane-5-carboxamide, 1-(3-methylcyclohexyl)-3-[6-(trifluoromethyl)-1,3-benzothiazol-2-yl]urea, 3,5-dimethyl-N-[6-(trifluoromethyl)-1,3-benzoxazol-2-yl]adamantane-1-carboxamide, N-(5,6-dichloro-1H-1,3-benzodiazol-2-yl)-3,3,5-trimethylcyclohexane-1-carboxamide, 3-methyl-N-[6-(trifluoromethyl)-1,3-benzothiazol-2-yl]cyclopentane-1-carboxamide, N-(5-bromo-1,3-benzothiazol-2-yl)-1-methylcyclopentane-1-carboxamide, 1-methyl-N-(4,5,6-trifluoro-1,3-benzothiazol-2-yl)cyclohexane-1-carboxamide, N-(1,3-benzoxazol-2-yl)adamantane-1- carboxamide, N-[6-(difluoromethoxy)-1,3-benzothiazol-2-yl]cyclohexanecarboxamide, N-(4,6-difluoro-1,3-benzothiazol-2-yl)cyclohexanecarboxamide, N-(6-bromo-1,3-benzoxazol-2-yl)-3,3,5-trimethylcyclohexane-1-carboxamide, N-(1,3-benzoxazol-2-yl)bicyclo[3.3.1]nonane-3-carboxamide, N-(1-benzothiophen-2-yl)cycloheptanecarboxamide, N-(5,7-dimethyl-1,3-benzoxazol-2-yl)-3,5-dimethyladamantane-1-carboxamide, N-(6-methoxy-1,3-benzoxazol-2-yl)-3,3,5-trimethylcyclohexane-1-carboxamide, 3,3,5-trimethyl-N-[6-(trifluoromethyl)-1,3-benzoxazol-2-yl]cyclohexane-1-carboxamide, N-(5,6-dichloro-1H-1,3-benzodiazol-2-yl)-3,5-dimethyladamantane-1-carboxamide, N-(1,3-benzoxazol-2-yl)-3,3,5-trimethylcyclohexane-1-carboxamide, N-(1,3-benzothiazol-2-yl)-2-methylcyclohexane-1-carboxamide, N-(4-chloro-1,3-benzothiazol-2-yl)-3-methylcyclohexane-1-carboxamide, N-(6-chloro-1,3-benzothiazol-2-yl)-3-methylcyclohexane-1-carboxamide, N-(4,6-difluoro-1,3-benzothiazol-2-yl)-3-methylcyclohexane-1-carboxamide, N-(6-fluoro-1,3-benzothiazol-2-yl)-3-methylcyclohexane-1-carboxamide, N-(4,6-difluoro-1,3-benzothiazol-2-yl)-1-methylcyclohexane-1-carboxamide, N-[6-(difluoromethoxy)-1,3-benzothiazol-2-yl]-1-methylcyclohexane-1-carboxamide, 2,2-dimethyl-N-[6-(trifluoromethoxy)-1,3-benzothiazol-2-yl]propanamide, N-(7-hydroxy-1,3-benzothiazol-2-yl)-3,3,5-trimethylcyclohexane-1-carboxamide, N-(5,6-difluoro-1,3-benzoxazol-2-yl)-3,3,5-trimethylcyclohexane-1-carboxamide, N-(1-benzothiophen-2-yl)cyclohexanecarboxamide, 3,3,5-trimethyl-N-{6-[(trifluoromethyl)sulfanyl]-1,3-benzothiazol-2-yl}cyclohexane-1-carboxamide, N-(6-fluoro-1H-1,3-benzodiazol-2-yl)-3,3,5-trimethylcyclohexane-1-carboxamide, N-(4-chloro-1,3-benzothiazol-2-yl)-3,3,5-trimethylcyclohexane-1-carboxamide, 3-methyl-N-(4-methyl-1,3-benzothiazol-2-yl)cyclohexane-1-carboxamide, N-(6-methoxy-1,3-benzothiazol-2-yl)-3-methylcyclohexane-1-carboxamide, N-(1,3-benzothiazol-2-yl)-3-methylcyclohexane-1-carboxamide, N-(4-methyl-1,3-benzothiazol-2-yl)bicyclo[2.2.1]heptane-2-carboxamide, N-(5,7-dichloro-1,3-benzoxazol-2-yl)-5-methylbicyclo[3.3.1]nonane-1-carboxamide, 2-methyl-N-[6-(trifluoromethoxy)-1,3-benzothiazol-2-yl]-7-oxabicyclo[2.2.1]heptane-2-carboxamide, N-[6-(dimethylamino)-1,3-benzothiazol-2-yl]-3,3,5-trimethylcyclohexane-1-carboxamide, N-(1,3-benzoxazol-2-yl)cyclooctanecarboxamide, N-[6-(trifluoromethoxy)-1,3-benzothiazol-2-yl]cyclohexanecarboxamide, N-(4,6-difluoro-1,3-benzoxazol-2-yl)-3,3,5-trimethylcyclohexane-1-carboxamide, N-(5-bromo-1,3-benzothiazol-2-yl)-3,3,5-trimethylcyclohexane-1-carboxamide, N-(6-chloro-1,3-benzothiazol-2-yl)-3-methoxycyclohexane-1-carboxamide, N-[6-(trifluoromethyl)-1,3-benzothiazol-2-yl]spiro[2.5]octane-6-carboxamide.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

When used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

When used herein, the term "hydrate" is a solvate wherein the solvent molecule is $H_2O$.

As used herein, the phrases "effective amount" or "therapeutically effective amount" are meant to describe an amount of compound or a composition of the present invention effective in inhibiting bacterial replication and thus producing the desired therapeutic, ameliorative, inhibitory or preventative effect.

The compounds of Formula (I) (as defined herein Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates, or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g.

decyl, lauryl, and stearyl chlorides, bromides and iodides), arylalkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula (I) and salts, solvates and prodrugs thereof, may exist in their tautomeric form (for example, as an amide or imino ether). All such tautomeric forms are contemplated herein as part of the present invention. All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Another aspect of this invention is a method of protecting a patient from a mycobacterial infection. A patient may be an animal, preferably a mammal and even more preferably a human having or susceptible to a disease or condition associated with a bacterial infection. Protecting may be prophylactic, i.e., administering a compound of the present invention in the absence of a diagnosed bacterial infection, or therapeutic, i.e., administering a compound of the present invention upon diagnosis of a bacterial infection. Protection may be achieved by administering a therapeutically effective amount of at least one compound of Formula (I), or a pharmaceutically acceptable salt or solvate of said compound to the patient. A preferred dosage is about 0.001 to 500 mg/kg of body weight/day of the compound of Formula (I) or a pharmaceutically acceptable salt or solvate of said compound. An especially preferred dosage is about 0.01 to 25 mg/kg of body weight/day of a compound of Formula (I), or a pharmaceutically acceptable salt or solvate of said compound.

Methods to diagnose bacterial infection in patients are known in the art. Preferred bacterial infections to treat include bacterial infections caused by any bacteria type or species against which the compounds of the present invention have an antimycobacterial effect. Particularly preferred bacteria types or species include Gram-positive and Gram-negative bacteria and most preferred bacterial types include Gram-positive bacteria.

In order to protect an animal from bacterial infection, a therapeutic or prophylactic composition of the present invention is administered to the animal in an effective manner such that bacterial infection is minimized and/or reduced. Preferably, the bacterial infection and/or bacterial burden of the infectious bacteria is reduced by at least about 50%, at least about 70%, and more preferably at least about 90%, 95% or 97%.

Suitable patients to treat include humans; birds such as chickens, ostriches, quail, and turkeys; other mammals such as companion animals (including dogs, cats, and rodents) and economic food and/or fur or other product animals, such as horses, cattle, llamas, chinchillas, ferrets, goats, sheep, rodents, minks, rabbits, raccoons, and swine.

The compounds of this invention can also be useful in combination (administered together or sequentially) with one or more of antimycobacterial treatments, such as, for example, treatment with other known antibacterial drug classes such as, for example, β-lactams, glycopeptides, oxazolidinones, macrolides, ketolides, quinolones, fluoroquinolones, aminoglycosides, tetracyclines, and lipopeptides. If formulated as a fixed dose, such combination products employ the compounds of this invention within the dosage range described herein and the other pharmaceutically active agent or treatment within its dosage range. Compounds of Formula (I) may also be administered sequentially with known antibacterial agents when a combination formulation is inappropriate. The invention is not limited in the sequence of administration; compounds of Formula (I) may be administered either prior to or after administration of the known antibacterial agent. Such techniques are within the skills of persons skilled in the art as well as attending physicians.

Accordingly, in an aspect, this invention includes combinations comprising an amount of at least one compound of Formula (I), or a pharmaceutically acceptable salt or solvate thereof, and an amount of one or more antibacterial agents or treatments listed above wherein the amounts of the compounds/treatments result in desired therapeutic effect. The pharmacological properties of the compounds of this invention may be confirmed by a number of pharmacological assays. The exemplified pharmacological assays which are described herein have been carried out with compounds according to the invention and/or their salts.

In another aspect, the invention includes pharmaceutical compositions which comprise at least one compound of Formula (I), or a pharmaceutically acceptable salt or solvate of said compound, and at least one pharmaceutically acceptable carrier. Accordingly, the present invention further includes compositions comprising one or more compounds of Formula (I) and a pharmaceutically acceptable carrier.

When used herein, the phrase "pharmaceutically acceptable carrier" refers to media generally accepted in the art for the delivery of biologically active agents to patients, in particular, mammals. Pharmaceutically acceptable carriers are typically formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th ed., Mack Publishing Company, Easton, Pa., 1985, which is incorporated herein by reference in its entirety.

Preparation of pharmaceutical compositions of the invention include inclusion of inert, solid or liquid pharmaceutically acceptable carriers. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, silica, sucrose, lactose, starch, or cellulose derivatives. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example, water or water-propylene glycol solutions for parenteral injection or addition of sweeteners and opacifiers for oral solutions, suspensions and emulsions, can be used. Liquid form preparations may also include solutions for intranasal administration. Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract. Liquid dose forms for oral administration can also contain coloring or flavoring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water-soluble salt of the active ingredient and suitable stabilizing agent(s). Antioxidizing agents, such as sodium bisulfite, sodium sulfite, or ascorbic acid, either alone or in combination, can act as suitable stabilizing agents. Also suitable as stabilizing agents are citric acid and its salts, and EDTA. In addition, parenteral solutions can contain preservatives such as, for example, benzalkonium chloride, methyl- or propyl-paraben, and chlorobutanol.

Inhilation compositions are preferred and will generally include an inert diluent or a carrier and may be prepared as dry powder inhaler or solution/suspension. The inhaled dosage forms are administered to the patient weekly, twice weekly, three times weekly, four times weekly, five times weekly, six times weekly, or 1, 2, 3, or 4 times daily. It is preferred that the compounds of the invention be administered either three or fewer times daily, more preferably once or twice daily. For purposes of oral therapeutic administration, the active compound or compounds can be incorporated with excipients and used in the form of tablets, capsules, lozenges, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes, colorings, and flavors. The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known, for example, as described in U.S. Pat. No. 4,522,811, which is incorporated by reference herein.

The active compounds may be prepared with carriers that protect the compound against rapid elimination from the body, such as time-release formulations or coatings such as enteric coatings to protect the compounds of the present invention from the acidic environment of the stomach. Enteric coated tablets are well known to those skilled in the art. In addition, capsules filled with small spheres, each coated to protect from the acidic stomach, are also well known to those skilled in the art. Other such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered via intrapulmonary routes, orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

When administered via intrapulmonary routes, compounds of the invention can be administered in usual dosage forms for inhaled administration as is well known to those skilled in the art and are described more fully herein. These dosage forms include the drypower inhaler and nebulizer using solution or suspension.

The compounds of the invention can be administered parenterally, for example, by IV, IM, depo-IM, SC, or depo-SC. When administered parenterally, a therapeutically effective amount for humans of about 0.5 to about 100 mg/day, preferably from about 5 to about 50 mg daily should be delivered. When a depot formulation is used for injection once a month or once every two weeks, the dose for humans should be about 0.5 mg/day to about 50 mg/day, or a monthly dose of from about 15 mg to about 1,500 mg. Dosing for other types of patients can be estimated from the appropriate human dose.

The compounds of the invention can be administered sublingually. When given sublingually, the compounds of the invention should be given one to four times daily in the amounts described above for IM administration.

The compounds of the invention can also be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenteral dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. When administered topically, the dosage is from about 0.5 mg/day to about 200 mg/day. The compounds of the invention can be administered rectally by suppository as is known to those skilled in the art. When administered by suppository, the therapeutically effective amount is from about 0.5 mg to about 500 mg for humans. The compounds of the invention can be administered by implants as is known to those skilled in the art. When administering a compound of the invention by implant, the therapeutically effective amount is the amount described above for depot administration.

In one aspect, the invention herein includes the novel compounds and new methods of using the compounds of the invention. Given a particular compound of the invention and a desired dosage form, one skilled in the art would know how to prepare and administer the appropriate dosage form.

Where the compounds of the invention exhibit insufficient solubility, methods for solubilizing may be used. Such methods are known and include, but are not limited to, using cosolvents such as dimethylsulfoxide (DMSO), using surfactants such as polysorbates including Tween® and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration. A suitable single dose is a dose that is capable of reducing bacterial infection and/or bacterial burden with the infectious bacteria when administered one or more times over a suitable time period. For example, a preferred single dose of a compound of Formula (I) ranges from about 1 microgram to about 10 milligrams, but can range up to 100 milligrams of the composition per kilogram body weight of the patient.

The active compound is typically included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound of the invention in lyophilized form, and a suitable diluent, may be provided as separated components for combination prior to use. A kit may include a compound of the invention and a second therapeutic agent for co-administration. The compound of the invention and second therapeutic agent may be provided as separate component parts.

A kit herein may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, ointments, and the like for topical administration.

The concentration of active compound in the drug composition will depend on absorption, inactivation, and excretion rates of the active compound, the dosage schedule, and amount administered as well as other factors known to those of skill in the art. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data.

It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the composition(s), and that the concentration ranges set forth herein are exemplary only and are not intended to limit the scope or practice of the claimed compositions.

Compounds of the invention can be prepared as described in the following Examples.

The invention disclosed herein is exemplified by the following preparations and examples which should not be construed to limit the scope of the disclosure. Alternative mechanistic pathways and analogous structures will be apparent to those skilled in the art.

EXAMPLES

The following abbreviations are used throughout the Example section and are not meant to limit the scope of the disclosure.

TLC=thin layer chromatography
eq.=equivalents
equiv.=equivalents
THF=tetrahydrofuran
DIPEA=diisopropylethylamine
DIEA=diisopropylethylamine
DCM=dichloromethane
MeOH=methanol
EtOAc=ethyl acetate
BOC$_2$O=di-tert-butyl dicarbonate
mCPBA=3-chloroperbenzoic acid
DMAP=4-(Dimethylamino)pyridine
TFA=trifluoroacetic acid
DMA=N,N-dimethylacetamide
TBTU=O-(Benzotriazol-1-yl)-N,N,N',N'-tetramethyluronium tetrafluoroborate
DMSO=dimethyl sulfoxide
Et$_2$O=diethyl ether
MeCN=acetonitrile
DMF=N, N-dimethylformamide
NMP=1-Methyl-2-pyrrolidinone
DAST=(Diethylamino)sulfur trifluoride
DCE=1,2-dichloroethane The compounds of Examples 1-192 shown below in Tables 1 were prepared by the methods described in method 1.

TABLE 1

Preparation of compounds in formula I

| Example # | Compound # | IUPAC | MW (g/mol) | ESI+ (g/mol) | Chemical formula | Method |
|---|---|---|---|---|---|---|
| 1 | 1 | N-(1-benzothiophen-2-yl)-5-methylbicyclo[3.3.1]nonane-1-carboxamide | 313 | 314 | C19H23NOS | 1 |
| 2 | 2 | N-(5,7-dichloro-1,3-benzothiazol-2-yl)-5-methylbicyclo[3.3.1]nonane-1-carboxamide | 383 | 384 | C18H20Cl2N2OS | 1 |
| 3 | 3 | N-(5-bromo-1,3-benzothiazol-2-yl)-5-methylbicyclo[3.3.1]nonane-1-carboxamide | 393 | 394 | C18H21BrN2OS | 1 |
| 4 | 4 | N-(5,7-difluoro-1,3-benzothiazol-2-yl)-5-methylbicyclo[3.3.1]nonane-1-carboxamide | 350 | 351 | C18H20F2N2OS | 1 |
| 5 | 5 | 5-methyl-N-[6-(trifluoromethoxy)-1,3-benzothiazol-2-yl]bicyclo[3.3.1]nonane-1-carboxamide | 398 | 399 | C19H21F3N2O2S | 1 |
| 6 | 6 | 1-methyl-N-[6-(trifluoromethoxy)-1,3-benzothiazol-2-yl]cycloheptane-1-carboxamide | 372 | 373 | C17H19F3N2O2S | 1 |
| 7 | 7 | N-[6-(trifluoromethoxy)-1,3-benzothiazol-2-yl]adamantane-2-carboxamide | 396 | 397 | C19H19F3N2O2S | 1 |
| 8 | 8 | N-(5,7-dimethyl-1,3-benzothiazol-2-yl)-5-methylbicyclo[3.3.1]nonane-1-carboxamide | 343 | 344 | C20H26N2OS | 1 |
| 9 | 9 | 5-methyl-N-(4,5,6-trifluoro-1,3-benzothiazol-2-yl)bicyclo[3.3.1]nonane-1-carboxamide | 368 | 369 | C18H19F3N2OS | 1 |
| 10 | 10 | N-(4,6-difluoro-1,3-benzothiazol-2-yl)-5-methylbicyclo[3.3.1]nonane-1-carboxamide | 350 | 351 | C18H20F2N2OS | 1 |
| 11 | 11 | N-(6-bromo-1,3-benzothiazol-2-yl)-5-methylbicyclo[3.3.1]nonane-1-carboxamide | 393 | 394 | C18H21BrN2OS | 1 |
| 12 | 12 | N-(6-chloro-1,3-benzothiazol-2-yl)-5-methylbicyclo[3.3.1]nonane-1-carboxamide | 349 | 350 | C18H21ClN2OS | 1 |
| 13 | 13 | N-[6-(difluoromethoxy)-1,3-benzothiazol-2-yl]-5-methylbicyclo[3.3.1]nonane-1-carboxamide | 380 | 381 | C19H22F2N2O2S | 1 |
| 14 | 14 | (3R,5S,7s)-N-[6-(trifluoromethoxy)-1,3-benzothiazol-2-yl]adamantane-1-carboxamide | 396 | 397 | C19H19F3N2O2S | 1 |
| 15 | 15 | N-[6-(trifluoromethoxy)-1,3-benzothiazol-2-yl]bicyclo[3.3.1]nonane-3-carboxamide | 384 | 385 | C18H19F3N2O2S | 1 |
| 16 | 16 | N-[6-(trifluoromethoxy)-1,3-benzothiazol-2-yl]-decahydronaphthalene-2-carboxamide | 398 | 399 | C19H21F3N2O2S | 1 |
| 17 | 17 | (1R,3S)-1,2,2,3-tetramethyl-N-[6-(trifluoromethoxy)-1,3-benzothiazol-2-yl]cyclopentane-1-carboxamide | 386 | 387 | C18H21F3N2O2S | 1 |
| 18 | 18 | N-(5,7-dichloro-1,3-benzothiazol-2-yl)-1-methylcycloheptane-1-carboxamide | 357 | 358 | C16H18Cl2N2OS | 1 |
| 19 | 19 | N-(1-benzothiophen-2-yl)adamantane-2-carboxamide | 311 | 312 | C19H21NOS | 1 |
| 20 | 20 | N-(5,7-dichloro-1,3-benzothiazol-2-yl)adamantane-2-carboxamide | 381 | 382 | C18H18Cl2N2OS | 1 |
| 21 | 21 | 5-methyl-N-[6-(trifluoromethyl)-1,3-benzothiazol-2-yl]bicyclo[3.3.1]nonane-1-carboxamide | 382 | 383 | C19H21F3N2OS | 1 |
| 22 | 22 | 1,3-dimethyl-N-[6-(trifluoromethoxy)-1,3-benzothiazol-2-yl]cyclopentane-1-carboxamide | 358 | 359 | C16H17F3N2O2S | 1 |
| 23 | 23 | N-(5,7-dichloro-1,3-benzothiazol-2-yl)-1-methylcyclohexane-1-carboxamide | 343 | 344 | C15H16Cl2N2OS | 1 |
| 24 | 24 | N-(5-bromo-1-benzothiophen-2-yl)-3,5-dimethyladamantane-1-carboxamide | 418 | 419 | C21H24BrNOS | 1 |
| 25 | 25 | 3,3,5-trimethyl-N-[5-(trifluoromethyl)-1,3-benzothiazol-2-yl]cyclohexane-1-carboxamide | 370 | 371 | C18H21F3N2OS | 1 |
| 26 | 26 | N-(1-benzothiophen-2-yl)adamantane-1-carboxamide | 311 | 312 | C19H21NOS | 1 |
| 27 | 27 | 1-ethyl-N-[6-(trifluoromethoxy)-1,3-benzothiazol-2-yl]cyclohexane-1-carboxamide | 372 | 373 | C17H19F3N2O2S | 1 |
| 28 | 28 | 1-methyl-N-[6-(trifluoromethoxy)-1,3-benzothiazol-2-yl]cyclohexane-1-carboxamide | 358 | 359 | C16H17F3N2O2S | 1 |
| 29 | 29 | N-[6-(trifluoromethoxy)-1,3-benzothiazol-2-yl]tricyclo[3.3.1.0³,⁷]nonane-3-carboxamide | 382 | 383 | C18H17F3N2O2S | 1 |
| 30 | 30 | (3R,5S,7s)-N-(4,5,6-trifluoro-1,3-benzothiazol-2-yl)adamantane-1-carboxamide | 366 | 367 | C18H17F3N2OS | 1 |
| 31 | 31 | N-(5,7-difluoro-1,3-benzothiazol-2-yl)-3,5-dimethyladamantane-1-carboxamide | 376 | 377 | C20H22F2N2OS | 1 |

TABLE 1-continued

Preparation of compounds in formula I

| Example # | Compound # | IUPAC | MW (g/mol) | ESI+ (g/mol) | Chemical formula | Method |
|---|---|---|---|---|---|---|
| 32 | 32 | N-(5,7-difluoro-1,3-benzothiazol-2-yl)-3,3,5-trimethylcyclohexane-1-carboxamide | 338 | 339 | C17H20F2N2OS | 1 |
| 33 | 33 | N-(4,6-difluoro-1,3-benzothiazol-2-yl)bicyclo[3.3.1]nonane-3-carboxamide | 336 | 337 | C17H18F2N2OS | 1 |
| 34 | 34 | N-(5,7-dichloro-1,3-benzothiazol-2-yl)-3,5-dimethyladamantane-1-carboxamide | 409 | 410 | C20H22Cl2N2OS | 1 |
| 35 | 35 | N-(5,7-dichloro-1,3-benzothiazol-2-yl)-3,3,5-trimethylcyclohexane-1-carboxamide | 371 | 372 | C17H20Cl2N2OS | 1 |
| 36 | 36 | N-[6-(trifluoromethoxy)-1,3-benzothiazol-2-yl]cyclooctanecarboxamide | 372 | 373 | C17H19F3N2O2S | 1 |
| 37 | 37 | N-(5-chloro-1,3-benzothiazol-2-yl)-3,5-dimethyladamantane-1-carboxamide | 375 | 376 | C20H23ClN2OS | 1 |
| 38 | 38 | N-(6-chloro-1,3-benzothiazol-2-yl)-3,5-dimethyladamantane-1-carboxamide | 375 | 376 | C20H23ClN2OS | 1 |
| 39 | 39 | (1R,3R,7r)-3,5-dimethyl-N-[6-(trifluoromethyl)-1,3-benzothiazol-2-yl]adamantane-1-carboxamide | 408 | 409 | C21H23F3N2OS | 1 |
| 40 | 40 | N-(1-benzothiophen-2-yl)bicyclo[3.3.1]nonane-3-carboxamide | 299 | 300 | C18H21NOS | 1 |
| 41 | 41 | N-(4,5,6-trifluoro-1,3-benzothiazo1-2-yl)bicyclo[3.3.1]nonane-3-carboxamide | 354 | 355 | C17H17F3N2OS | 1 |
| 42 | 42 | N-(1-benzothiophen-2-yl)-3,5-dimethyladamantane-1-carboxamide | 340 | 341 | C21H25NOS | 1 |
| 43 | 43 | N-(7-fluoro-1,3-benzothiazol-2-yl)-3,5-dimethyladamantane-1-carboxamide | 358 | 359 | C20H23FN2OS | 1 |
| 44 | 44 | N-(5,6-difluoro-1,3-benzothiazol-2-yl)-3,5-dimethyladamantane-1-carboxamide | 376 | 377 | C20H22F2N2OS | 1 |
| 45 | 45 | 3,5-dimethyl-N-[6-(trifluoromethoxy)-1,3-benzothiazol-2-yl]adamantane-1-carboxamide | 424 | 425 | C21H23F3N2O2S | 1 |
| 46 | 46 | 3,3,5-trimethyl-N-[6-(trifluoromethoxy)-1,3-benzothiazol-2-yl]cyclohexane-1-carboxamide | 386 | 387 | C18H21F3N2O2S | 1 |
| 47 | 47 | N-(1-benzothiophen-2-yl)-3,3,5-trimethylcyclohexane-1-carboxamide | 301 | 302 | C18H23NOS | 1 |
| 48 | 48 | N-(5-bromo-1,3-benzothiazol-2-yl)-3,5-dimethyladamantane-1-carboxamide | 419 | 420 | C20H23BrN2OS | 1 |
| 49 | 49 | N-(5,7-dichloro-1,3-benzothiazol-2-yl)-1-methylcyclopentane-1-carboxamide | 329 | 330 | C14H14Cl2N2OS | 1 |
| 50 | 50 | (1R,2R,4R)-2-methyl-N-[6-(trifluoromethoxy)-1,3-benzothiazol-2-yl]bicyclo[2.2.1]hept-5-ene-2-carboxamide | 368 | 369 | C17H15F3N2O2S | 1 |
| 51 | 51 | 3,3-dimethyl-N-[6-(trifluoromethoxy)-1,3-benzothiazol-2-yl]cyclopentane-1-carboxamide | 358 | 359 | C16H17F3N2O2S | 1 |
| 52 | 52 | 1-methyl-N-[6-(trifluoromethyl)-1,3-benzothiazol-2-yl]cycloheptane-1-carboxamide | 356 | 357 | C17H19F3N2OS | 1 |
| 53 | 53 | N-(5-bromo-1,3-benzothiazol-2-yl)-1-methylcycloheptane-1-carboxamide | 367 | 368 | C16H19BrN2OS | 1 |
| 54 | 54 | N-(1-benzothiophen-2-yl)-1-methylcycloheptane-1-carboxamide | 287 | 288 | C17H21NOS | 1 |
| 55 | 55 | N-(6-bromo-1,3-benzothiazol-2-yl)adamantane-2-carboxamide | 391 | 392 | C18H19BrN2OS | 1 |
| 56 | 56 | N-(6-chloro-1,3-benzothiazol-2-yl)adamantane-2-carboxamide | 347 | 348 | C18H19ClN2OS | 1 |
| 57 | 57 | N-(5,7-difluoro-1,3-benzothiazol-2-yl)adamantane-2-carboxamide | 348 | 349 | C18H18F2N2OS | 1 |
| 58 | 58 | N-(4,5,6-trifluoro-1,3-benzothiazol-2-yl)adamantane-2-carboxamide | 366 | 367 | C18H17F3N2OS | 1 |
| 59 | 59 | N-[6-(difluoromethoxy)-1,3-benzothiazol-2-yl]adamantane-2-carboxamide | 378 | 379 | C19H20F2N2O2S | 1 |
| 60 | 60 | 1,2-dimethyl-N-[6-(trifluoromethoxy)-1,3-benzothiazol-2-yl]cyclopentane-1-carboxamide | 358 | 359 | C16H17F3N2O2S | 1 |
| 61 | 61 | 3,5-dimethyl-N-[5-(trifluoromethyl)-1,3-benzothiazol-2-yl]adamantane-1-carboxamide | 408 | 409 | C21H23F3N2OS | 1 |
| 62 | 62 | N-(6-bromo-1,3-benzothiazol-2-yl)bicyclo[3.3.1]nonane-3-carboxamide | 379 | 380 | C17H19BrN2OS | 1 |
| 63 | 63 | N-[6-(difluoromethoxy)-1,3-benzothiazol-2-yl]bicyclo[3.3.1]nonane-3-carboxamide | 366 | 367 | C18H20F2N2O2S | 1 |
| 64 | 64 | N-(6-chloro-1,3-benzothiazol-2-yl)bicyclo[3.3.1]nonane-3-carboxamide | 335 | 336 | C17H19ClN2OS | 1 |
| 65 | 65 | N-(5,7-dimethyl-1,3-benzothiazol-2-yl)-3,3,5-trimethylcyclohexane-1-carboxamide | 330 | 331 | C19H26N2OS | 1 |
| 66 | 66 | N-(5,7-dichloro-1,3-benzoxazol-2-yl)-3,5-dimethyladamantane-1-carboxamide | 393 | 394 | C20H22Cl2N2O2 | 1 |
| 67 | 67 | 3,5-dimethyl-N-{6-[(trifluoromethyl)sulfanyl]-1,3-benzothiazol-2-yl}adamantane-1-carboxamide | 441 | 442 | C21H23F3N2OS2 | 1 |
| 68 | 68 | N-[6-(difluoromethoxy)-1,3-benzothiazol-2-yl]-3,5-dimethyladamantane-1-carboxamide | 406 | 407 | C21H24F2N2O2S | 1 |
| 69 | 69 | N-(6-bromo-4-fluoro-1,3-benzothiazol-2-yl)-3,5-dimethyladamantane-1-carboxamide | 437 | 438 | C20H22BrFN2OS | 1 |
| 70 | 70 | N-(5-fluoro-1,3-benzothiazol-2-yl)-3,5-dimethyladamantane-1-carboxamide | 358 | 359 | C20H23FN2OS | 1 |
| 71 | 71 | N-(4,6-difluoro-1,3-benzothiazol-2-yl)-3,5-dimethyladamantane-1-carboxamide | 376 | 377 | C20H22F2N2OS | 1 |
| 72 | 72 | N-(7-fluoro-1,3-benzothiazol-2-yl)-3,3,5-trimethylcyclohexane-1-carboxamide | 320 | 321 | C17H21FN2OS | 1 |
| 73 | 73 | N-(6-bromo-1,3-benzothiazol-2-yl)-3,5-dimethyladamantane-1-carboxamide | 419 | 420 | C20H23BrN2OS | 1 |
| 74 | 74 | N-(6-fluoro-1,3-benzothiazol-2-yl)-3,3,5-trimethylcyclohexane-1-carboxamide | 320 | 321 | C17H21FN2OS | 1 |
| 75 | 75 | N-(6-chloro-1,3-benzothiazol-2-yl)-3,3,5-trimethylcyclohexane-1-carboxamide | 337 | 338 | C17H21ClN2OS | 1 |

TABLE 1-continued

Preparation of compounds in formula I

| Example # | Compound # | IUPAC | MW (g/mol) | ESI+ (g/mol) | Chemical formula | Method |
|---|---|---|---|---|---|---|
| 76 | 76 | N-(6-bromo-1,3-benzothiazol-2-yl)-3,3,5-trimethylcyclohexane-1-carboxamide | 381 | 382 | C17H21BrN2OS | 1 |
| 77 | 77 | 3,3,5-trimethyl-N-(4,5,6-trifluoro-1,3-benzothiazol-2-yl)cyclohexane-1-carboxamide | 356 | 357 | C17H19F3N2OS | 1 |
| 78 | 78 | 3,5-dimethyl-N-[6-(trifluoromethyl)-1,3-benzothiazol-2-yl]adamantane-1-carboxamide | 408 | 409 | C21H23F3N2OS | 1 |
| 79 | 79 | 3,3,5-trimethyl-N-[6-(trifluoromethyl)-1,3-benzothiazol-2-yl]cyclohexane-1-carboxamide | 370 | 371 | C18H21F3N2OS | 1 |
| 80 | 80 | N-(4,6-difluoro-1,3-benzothiazol-2-yl)-3,3,5-trimethylcyclohexane-1-carboxamide | 338 | 339 | C17H20F2N2OS | 1 |
| 81 | 81 | 3,3-difluoro-1-methyl-N-[6-(trifluoromethoxy)-1,3-benzothiazol-2-yl]cyclopentane-1-carboxamide | 380 | 381 | C15H13F5N2O2S | 1 |
| 82 | 82 | N-(4,6-difluoro-1,3-benzothiazol-2-yl)adamantane-2-carboxamide | 348 | 349 | C18H18F2N2OS | 1 |
| 83 | 83 | N-(5,7-dimethyl-1,3-benzothiazol-2-yl)adamantane-2-carboxamide | 340 | 341 | C20H24N2OS | 1 |
| 84 | 84 | 1-methyl-N-[6-(trifluoromethyl)-1,3-benzothiazol-2-yl]cyclohexane-1-carboxamide | 342 | 343 | C16H17F3N2OS | 1 |
| 85 | 85 | 1-(2-methylpropyl)-N-[6-(trifluoromethoxy)-1,3-benzothiazol-2-yl]cyclopentane-1-carboxamide | 386 | 387 | C18H21F3N2O2S | 1 |
| 86 | 86 | N-(4,6-difluoro-1,3-benzothiazol-2-yl)adamantane-1-carboxamide | 348 | 349 | C18H18F2N2OS | 1 |
| 87 | 87 | N-[6-(difluoromethoxy)-1,3-benzothiazol-2-yl]adamantane-1-carboxamide | 378 | 379 | C19H20F2N2O2S | 1 |
| 88 | 88 | N-(5,6-difluoro-1,3-benzoxazol-2-yl)-3,5-dimethyladamantane-1-carboxamide | 360 | 361 | C20H22F2N2O2 | 1 |
| 89 | 89 | N-(1-benzothiophen-2-yl)cyclooctanecarboxamide | 287 | 288 | C17H21NOS | 1 |
| 90 | 90 | N-(5,7-dimethyl-1,3-benzothiazol-2-yl)-3,5-dimethyladamantane-1-carboxamide | 369 | 370 | C22H28N2OS | 1 |
| 91 | 91 | N-[6-(difluoromethoxy)-1,3-benzothiazol-2-yl]-3,3,5-trimethylcyclohexane-1-carboxamide | 368 | 369 | C18H22F2N2O2S | 1 |
| 92 | 92 | N-(6-bromo-4-fluoro-1,3-benzothiazol-2-yl)-3,3,5-trimethylcyclohexane-1-carboxamide | 399 | 400 | C17H20BrFN2OS | 1 |
| 93 | 93 | N-(5-fluoro-1,3-benzothiazol-2-yl)-3,3,5-trimethylcyclohexane-1-carboxamide | 320 | 321 | C17H21FN2OS | 1 |
| 94 | 94 | N-(1,3-benzothiazol-2-yl)-3,5-dimethyladamantane-1-carboxamide | 340 | 341 | C20H24N2OS | 1 |
| 95 | 95 | N-(4-chloro-1,3-benzothiazol-2-yl)-3,5-dimethyladamantane-1-carboxamide | 375 | 376 | C20H23ClN2OS | 1 |
| 96 | 96 | N-(6-methoxy-1,3-benzothiazol-2-yl)-3,3,5-trimethylcyclohexane-1-carboxamide | 332 | 333 | C18H24N2O2S | 1 |
| 97 | 97 | N-(4,6-dichloro-1,3-benzothiazol-2-yl)-3,5-dimethyladamantane-1-carboxamide | 409 | 410 | C20H22Cl2N2OS | 1 |
| 98 | 98 | 3,5-dimethyl-N-(6-methyl-1,3-benzothiazol-2-yl)adamantane-1-carboxamide | 355 | 356 | C21H26N2OS | 1 |
| 99 | 99 | 3,5-dimethyl-N-[6-(trifluoromethyl)-1,3-benzothiazol-2-yl]cyclohexane-1-carboxamide | 356 | 357 | C17H19F3N2OS | 1 |
| 100 | 100 | ethyl 2-(3,5-dimethyladamantane-1-amido)-1,3-benzothiazole-6-carboxylate | 413 | 414 | C23H28N2O3S | 1 |
| 101 | 101 | 1-ethyl-N-[6-(trifluoromethoxy)-1,3-benzothiazol-2-yl]cyclopentane-1-carboxamide | 358 | 359 | C16H17F3N2O2S | 1 |
| 102 | 102 | 3-methyl-N-[6-(trifluoromethoxy)-1,3-benzothiazol-2-yl]cyclopentane-1-carboxamide | 344 | 345 | C15H15F3N2O2S | 1 |
| 103 | 103 | 1-methyl-N-(4,5,6-trifluoro-1,3-benzothiazol-2-yl)cycloheptane-1-carboxamide | 342 | 343 | C16H17F3N2OS | 1 |
| 104 | 104 | 2-methyl-N-[6-(trifluoromethoxy)-1,3-benzothiazol-2-yl]bicyclo[2.2.1]heptane-2-carboxamide | 370 | 371 | C17H17F3N2O2S | 1 |
| 105 | 105 | N-(1-benzothiophen-2-yl)-1-methylcyclohexane-1-carboxamide | 273 | 274 | C16H19NOS | 1 |
| 106 | 106 | N-(6-bromo-5,7-dimethyl-1,3-benzothiazol-2-yl)-1-methylcyclohexane-1-carboxamide | 381 | 382 | C17H21BrN2OS | 1 |
| 107 | 107 | N-(6-chloro-1,3-benzothiazol-2-yl)adamantane-1-carboxamide | 347 | 348 | C18H19ClN2OS | 1 |
| 108 | 108 | N-[6-(difluoromethoxy)-1,3-benzothiazol-2-yl]cyclooctanecarboxamide | 354 | 355 | C17H20F2N2O2S | 1 |
| 109 | 109 | N-(4,6-difluoro-1,3-benzothiazol-2-yl)cyclooctanecarboxamide | 324 | 325 | C16H18F2N2OS | 1 |
| 110 | 110 | N-(6-chloro-1,3-benzothiazol-2-yl)cyclooctanecarboxamide | 323 | 324 | C16H19ClN2OS | 1 |
| 111 | 111 | N-(6-ethoxy-1,3-benzothiazol-2-yl)-3,5-dimethyladamantane-1-carboxamide | 385 | 386 | C22H28N2O2S | 1 |
| 112 | 112 | N-(5,6-dichloro-1,3-benzoxazol-2-yl)-3,5-dimethyladamantane-1-carboxamide | 393 | 394 | C20H22Cl2N2O2 | 1 |
| 113 | 113 | N-(5,6-dichloro-1,3-benzoxazol-2-yl)-3,3,5-trimethylcyclohexane-1-carboxamide | 355 | 356 | C17H20Cl2N2O2 | 1 |
| 114 | 114 | N-(5-chloro-1,3-benzoxazol-2-yl)-3,3,5-trimethylcyclohexane-1-carboxamide | 321 | 322 | C17H21ClN2O2 | 1 |
| 115 | 115 | N-(6-bromo-1,3-benzoxazol-2-yl)-3,5-dimethyladamantane-1-carboxamide | 403 | 404 | C20H23BrN2O2 | 1 |
| 116 | 116 | N-(4,5,6-trifluoro-1,3-benzothiazol-2-yl)cyclooctanecarboxamide | 342 | 343 | C16H17F3N2OS | 1 |
| 117 | 117 | N-(6-chloro-1,3-benzoxazol-2-yl)-3,5-dimethyladamantane-1-carboxamide | 359 | 360 | C20H23ClN2O2 | 1 |
| 118 | 118 | N-(6-chloro-1,3-benzoxazol-2-yl)-3,3,5-trimethylcyclohexane-1-carboxamide | 321 | 322 | C17H21ClN2O2 | 1 |
| 119 | 119 | N-(5,6-difluoro-1H-1,3-benzodiazol-2-yl)-3,5-dimethyladamantane-1-carboxamide | 359 | 360 | C20H23F2N3O | 1 |
| 120 | 120 | N-(6-fluoro-1H-1,3-benzodiazol-2-yl)-3,5-dimethyladamantane-1-carboxamide | 341 | 342 | C20H24FN3O | 1 |
| 121 | 121 | N-(4-fluoro-1,3-benzothiazol-2-yl)-3,3,5-trimethylcyclohexane-1-carboxamide | 320 | 321 | C17H21FN2OS | 1 |
| 122 | 122 | N-(4-fluoro-1,3-benzothiazol-2-yl)-3,5-dimethyladamantane-1-carboxamide | 358 | 359 | C20H23FN2OS | 1 |
| 123 | 123 | N-(6-fluoro-1,3-benzothiazol-2-yl)-3,5-dimethyladamantane-1-carboxamide | 358 | 359 | C20H23FN2OS | 1 |
| 124 | 124 | N-(6-methoxy-1,3-benzothiazol-2-yl)-3,5-dimethyladamantane-1-carboxamide | 371 | 372 | C21H26N2O2S | 1 |

TABLE 1-continued

Preparation of compounds in formula I

| Example # | Compound # | IUPAC | MW (g/mol) | ESI+ (g/mol) | Chemical formula | Method |
|---|---|---|---|---|---|---|
| 125 | 125 | N-(1,3-benzothiazol-2-yl)-3,3,5-trimethylcyclohexane-1-carboxamide | 302 | 303 | C17H22N2OS | 1 |
| 126 | 126 | 3-(trifluoromethyl)-N-[6-(trifluoromethyl)-1,3-benzothiazol-2-yl]cyclohexane-1-carboxamide | 396 | 397 | C16H14F6N2OS | 1 |
| 127 | 127 | 3-methyl-N-[6-(trifluoromethyl)-1,3-benzothiazol-2-yl]cyclohexane-1-carboxamide | 342 | 343 | C16H17F3N2OS | 1 |
| 128 | 128 | 1-methyl-N-[6-(trifluoromethyl)-1,3-benzothiazol-2-yl]cyclopentane-1-carboxamide | 328 | 329 | C15H15F3N2OS | 1 |
| 129 | 129 | (1R,2S,4R)-2-methyl-N-[6-(trifluoromethoxy)-1,3-benzothiazol-2-yl]bicyclo[2.2.1]hept-5-ene-2-carboxamide | 368 | 369 | C17H15F3N2O2S | 1 |
| 130 | 130 | N-[6-(trifluoromethoxy)-1,3-benzothiazol-2-yl]cyclopentanecarboxamide | 330 | 331 | C14H13F3N2O2S | 1 |
| 131 | 131 | N-(1,3-benzoxazol-2-yl)adamantane-2-carboxamide | 296 | 297 | C18H20N2O2 | 1 |
| 132 | 132 | 5-methyl-N-[6-(trifluoromethyl)-1,3-benzoxazol-2-yl]bicyclo[3.3.1]nonane-1-carboxamide | 366 | 367 | C19H21F3N2O2 | 1 |
| 133 | 133 | N-(5,7-difluoro-1,3-benzothiazol-2-yl)-1-methylcyclohexane-1-carboxamide | 310 | 311 | C15H16F2N2OS | 1 |
| 134 | 134 | N-(6-bromo-1,3-benzothiazol-2-yl)-1-methylcyclohexane-1-carboxamide | 353 | 354 | C15H17BrN2OS | 1 |
| 135 | 135 | N-(6-chloro-1,3-benzothiazol-2-yl)-1-methylcyclohexane-1-carboxamide | 309 | 310 | C15H17ClN2OS | 1 |
| 136 | 136 | 1-methyl-N-[6-(trifluoromethoxy)-1,3-benzothiazol-2-yl]cyclopentane-1-carboxamide | 344 | 345 | C15H15F3N2O2S | 1 |
| 137 | 137 | 3-methyl-N-[6-(trifluoromethoxy)-1,3-benzothiazol-2-yl]bicyclo[3.1.0]hexane-3-carboxamide | 356 | 357 | C16H15F3N2O2S | 1 |
| 138 | 138 | N-(6-ethoxy-1,3-benzothiazol-2-yl)bicyclo[3.3.1]nonane-3-carboxamide | 344 | 345 | C19H24N2O2S | 1 |
| 139 | 139 | N-(4,6-difluoro-1,3-benzothiazol-2-yl)cycloheptanecarboxamide | 310 | 311 | C15H16F2N2OS | 1 |
| 140 | 140 | N-(5-chloro-1,3-benzothiazol-2-yl)-3,5-dimethyladamantane-1-carboxamide | 359 | 360 | C20H23ClN2O2 | 1 |
| 141 | 141 | N-(4,5,6-trifluoro-1,3-benzothiazol-2-yl)cycloheptanecarboxamide | 328 | 329 | C15H15F3N2OS | 1 |
| 142 | 142 | N-(5,7-dichloro-1,3-benzoxazol-2-yl)-3,3,5-trimethylcyclohexane-1-carboxamide | 355 | 356 | C17H20Cl2N2O2 | 1 |
| 143 | 143 | N-(5,7-dimethyl-1,3-benzoxazol-2-yl)-3,3,5-trimethylcyclohexane-1-carboxamide | 314 | 315 | C19H26N2O2 | 1 |
| 144 | 144 | N-(4-fluoro-1,3-benzoxazol-2-yl)-3,5-dimethyladamantane-1-carboxamide | 342 | 343 | C20H23FN2O2 | 1 |
| 145 | 145 | N-(6-methoxy-1,3-benzoxazol-2-yl)-3,5-dimethyladamantane-1-carboxamide | 354 | 355 | C21H26N2O3 | 1 |
| 146 | 146 | N-(1H-1,3-benzodiazol-2-yl)-3,5-dimethyladamantane-1-carboxamide | 323 | 324 | C20H25N3O | 1 |
| 147 | 147 | N-(1,3-benzoxazol-2-yl)-3,5-dimethyladamantane-1-carboxamide | 324 | 325 | C20H24N2O2 | 1 |
| 148 | 148 | N-[6-(trifluoromethyl)-1,3-benzothiazol-2-yl]spiro[2.5]octane-5-carboxamide | 354 | 355 | C17H17F3N2OS | 1 |
| 149 | 149 | 1-(3-methylcyclohexyl)-3-[6-(trifluoromethyl)-1,3-benzothiazol-2-yl]urea | 357 | 358 | C16H18F3N3OS | 1 |
| 150 | 150 | 3,5-dimethyl-N-[6-(trifluoromethyl)-1,3-benzoxazol-2-yl]adamantane-1-carboxamide | 392 | 393 | C21H23F3N2O2 | 1 |
| 151 | 151 | N-(5,6-dichloro-1H-1,3-benzodiazol-2-yl)-3,3,5-trimethylcyclohexane-1-carboxamide | 354 | 355 | C17H21Cl2N3O | 1 |
| 152 | 152 | 3-methyl-N-[6-(trifluoromethyl)-1,3-benzothiazol-2-yl]cyclopentane-1-carboxamide | 328 | 329 | C15H15F3N2OS | 1 |
| 153 | 153 | N-(5-bromo-1,3-benzothiazol-2-yl)-1-methylcyclopentane-1-carboxamide | 339 | 340 | C14H15BrN2OS | 1 |
| 154 | 154 | 1-methyl-N-(4,5,6-trifluoro-1,3-benzothiazol-2-yl)cyclohexane-1-carboxamide | 328 | 329 | C15H15F3N2OS | 1 |
| 155 | 155 | N-(1,3-benzoxazol-2-yl)adamantane-1-carboxamide | 296 | 297 | C18H20N2O2 | 1 |
| 156 | 156 | N-[6-(difluoromethoxy)-1,3-benzothiazol-2-yl]cyclohexanecarboxamide | 326 | 327 | C15H16F2N2O2S | 1 |
| 157 | 157 | N-(4,6-difluoro-1,3-benzothiazol-2-yl)cyclohexanecarboxamide | 296 | 297 | C14H14F2N2OS | 1 |
| 158 | 158 | N-(6-bromo-1,3-benzoxazol-2-yl)-3,3,5-trimethylcyclohexane-1-carboxamide | 365 | 366 | C17H21BrN2O2 | 1 |
| 159 | 159 | N-(1,3-benzoxazol-2-yl)bicyclo[3.3.1]nonane-3-carboxamide | 284 | 285 | C17H20N2O2 | 1 |
| 160 | 160 | N-(1-benzothiophen-2-yl)cycloheptanecarboxamide | 273 | 274 | C16H19NOS | 1 |
| 161 | 161 | N-(5,7-dimethyl-1,3-benzoxazol-2-yl)-3,5-dimethyladamantane-1-carboxamide | 352 | 353 | C22H28N2O2 | 1 |
| 162 | 162 | N-(6-methoxy-1,3-benzoxazol-2-yl)-3,3,5-trimethylcyclohexane-1-carboxamide | 316 | 317 | C18H24N2O3 | 1 |
| 163 | 163 | 3,3,5-trimethyl-N-[6-(trifluoromethyl)-1,3-benzoxazol-2-yl]cyclohexane-1-carboxamide | 354 | 355 | C18H21F3N2O2 | 1 |
| 164 | 164 | N-(5,6-dichloro-1H-1,3-benzodiazol-2-yl)-3,5-dimethyladamantane-1-carboxamide | 392 | 393 | C20H23Cl2N3O | 1 |
| 165 | 165 | N-(1,3-benzoxazol-2-yl)-3,3,5-trimethylcyclohexane-1-carboxamide | 286 | 287 | C17H22N2O2 | 1 |
| 166 | 166 | N-(1,3-benzothiazol-2-yl)-2-methylcyclohexane-1-carboxamide | 274 | 275 | C15H18N2OS | 1 |
| 167 | 167 | N-(4-chloro-1,3-benzothiazol-2-yl)-3-methylcyclohexane-1-carboxamide | 309 | 310 | C15H17ClN2OS | 1 |
| 168 | 168 | N-(6-chloro-1,3-benzothiazol-2-yl)-3-methylcyclohexane-1-carboxamide | 309 | 310 | C15H17ClN2OS | 1 |
| 169 | 169 | N-(4,6-difluoro-1,3-benzothiazol-2-yl)-3-methylcyclohexane-1-carboxamide | 310 | 311 | C15H16F2N2OS | 1 |
| 170 | 170 | N-(6-fluoro-1,3-benzothiazol-2-yl)-3-methylcyclohexane-1-carboxamide | 292 | 293 | C15H17FN2OS | 1 |
| 171 | 171 | N-(4,6-difluoro-1,3-benzothiazol-2-yl)-1-methylcyclohexane-1-carboxamide | 310 | 311 | C15H16F2N2OS | 1 |
| 172 | 172 | N-[6-(difluoromethoxy)-1,3-benzothiazol-2-yl]-1-methylcyclohexane-1-carboxamide | 340 | 341 | C16H18F2N2O2S | 1 |
| 173 | 173 | 2,2-dimethyl-N-[6-(trifluoromethoxy)-1,3-benzothiazol-2-yl]propanamide | 318 | 319 | C13H13F3N2O2S | 1 |
| 174 | 174 | N-(7-hydroxy-1,3-benzothiazol-2-yl)-3,3,5-trimethylcyclohexane-1-carboxamide | 318 | 319 | C17H22N2O2S | 1 |
| 175 | 175 | N-(5,6-difluoro-1,3-benzoxazol-2-yl)-3,3,5-trimethylcyclohexane-1-carboxamide | 322 | 323 | C17H20F2N2O2 | 1 |
| 176 | 176 | N-(1-benzothiophen-2-yl)cyclohexanecarboxamide | 259 | 260 | C15H17NOS | 1 |
| 177 | 177 | 3,3,5-trimethyl-N-{6-[(trifluoromethyl)sulfanyl]-1,3-benzothiazol-2-yl}cyclohexane-1-carboxamide | 402 | 403 | C18H21F3N2OS2 | 1 |
| 178 | 178 | N-(6-fluoro-1H-1,3-benzodiazol-2-yl)-3,3,5-trimethylcyclohexane-1-carboxamide | 303 | 304 | C17H22FN3O | 1 |
| 179 | 179 | N-(4-chloro-1,3-benzothiazol-2-yl)-3,3,5-trimethylcyclohexane-1-carboxamide | 337 | 338 | C17H21ClN2OS | 1 |
| 180 | 180 | 3-methyl-N-(4-methyl-1,3-benzothiazol-2-yl)cyclohexane-1-carboxamide | 288 | 289 | C16H20N2OS | 1 |
| 181 | 181 | N-(6-methoxy-1,3-benzothiazol-2-yl)-3-methylcyclohexane-1-carboxamide | 304 | 305 | C16H20N2O2S | 1 |

TABLE 1-continued

Preparation of compounds in formula I

| Example # | Compound # | IUPAC | MW (g/mol) | ESI+ (g/mol) | Chemical formula | Method |
|---|---|---|---|---|---|---|
| 182 | 182 | N-(1,3-benzothiazol-2-yl)-3-methylcyclohexane-1-carboxamide | 274 | 275 | C15H18N2OS | 1 |
| 183 | 183 | N-(4-methyl-1,3-benzothiazol-2-yl)bicyclo[2.2.1]heptane-2-carboxamide | 286 | 287 | C16H18N2OS | 1 |
| 184 | 184 | N-(5,7-dichloro-1,3-benzoxazol-2-yl)-5-methylbicyclo[3.3.1]nonane-1-carboxamide | 367 | 368 | C18H20Cl2N2O2 | 1 |
| 185 | 185 | 2-methyl-N-[6-(trifluoromethoxy)-1,3-benzothiazol-2-yl]-7-oxabicyclo[2.2.1]heptane-2-carboxamide | 372 | 373 | C16H15F3N2O3S | 1 |
| 186 | 186 | N-[6-(dimethylamino)-1,3-benzothiazol-2-yl]-3,3,5-trimethylcyclohexane-1-carboxamide | 346 | 347 | C19H27N3OS | 1 |
| 187 | 187 | N-(1,3-benzoxazol-2-yl)cyclooctanecarboxamide | 272 | 273 | C16H20N2O2 | 1 |
| 188 | 188 | N-[6-(trifluoromethoxy)-1,3-benzothiazol-2-yl]cyclohexanecarboxamide | 344 | 345 | C15H15F3N2O2S | 1 |
| 189 | 189 | N-(4,6-difluoro-1,3-benzoxazol-2-yl)-3,3,5-trimethylcyclohexane-1-carboxamide | 322 | 323 | C17H20F2N2O2 | 1 |
| 190 | 190 | N-(5-bromo-1,3-benzothiazol-2-yl)-3,3,5-trimethylcyclohexane-1-carboxamide | 381 | 382 | C17H21BrN2OS | 1 |
| 191 | 191 | N-(6-chloro-1,3-benzothiazol-2-yl)-3-methoxycyclohexane-1-carboxamide | 325 | 326 | C15H17ClN2O2S | 1 |
| 192 | 192 | N-[6-(trifluoromethyl)-1,3-benzothiazol-2-yl]spiro[2.5]octane-6-carboxamide | 354 | 355 | C17H17F3N2OS | 1 |

Synthetic Methods for Compounds in Tables 1:
Method 1: Synthesis of Heterocyclic Amide Analogs

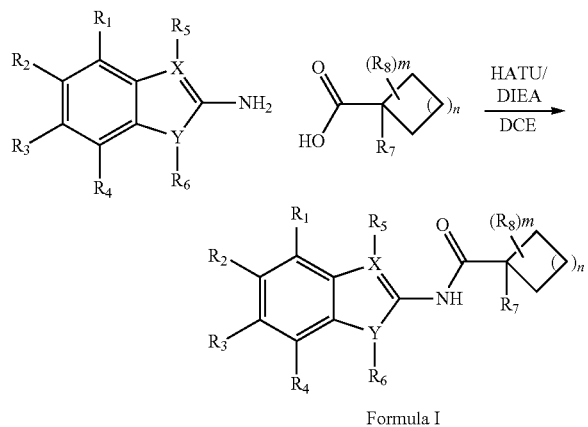

Formula I

Carboxylic acid (2 mmol, 1 equiv.) and HATU (76 mg, 0.2 mmol, 1 equiv.) were dissolved in 1 mL DCE in a one dram vial charged with a stir bar. DIPEA (0.1 mL, 0.6 mmol, 3 equiv.) was added and the resulting solution was stirred at RT for 10 minutes. Amine (0.2 mmol, 1 equiv.) was added to the mixture. The reaction solution was heated to 45° C. and stirred overnight. Upon completion the reaction mixture was condensed and loaded onto a 60 g C-18 cartridge and purified over a gradient of 5-95% ACN:H$_2$O. The fractions containing product were identified by LC-MS and condensed in vauco to give the final product.

Similar procedures were used to prepare other heterocyclic amide analogs from commercially available amines and carboxylic acids.

End of Method Section.

Example 193: Demonstration of Antimycobacterial Effect and Mechanism of Action

The assay for antimycobacterial activity against a variety of pathogenic organisms including M. abscessus, M. chelonae, M. fortuitum, M. peregrinum, M. avium, M. intracellulare, M. chimaera, and M. tuberculosis was carried out to determine minimum inhibitory concentrations (MICs). All compounds were tested using standard methods and conditions in accordance with CLSI guidelines (Clinical and Laboratory Standards Institute, document M24-A). Compounds described in the Examples 1-101 had MIC's of 0.03-1 µg/mL, 102-192 had MIC's of 2-32 µg/mL against M. abscessus, but were inactive (MIC>16 µg/mL against other pathogens, including S. aureus, S. pneumoniae, S. pyogenes, E. faecalis, E. coli, P. aeruginosa, and C. albicans. Compounds described in Examples 2 shown to be bactericidal against M. abscessus and M. tuberculosis.

Compounds of the present invention were not compromised by existing resistance to other drug classes tested, including macrolides, tetracylines, sulfamethoxazole, isoniazid, rifampin, and fluoroquinolones. In particular, compounds described in Examples 2, 5, 45, 46 and 80 were active against azithromycin-, doxycycline, and sulfamethoxazole-resistant M. abscessus, and against isoniazid-, rifampin-, and fluoroquinolone-resistant M. tuberculosis. MICs were comparable in drug-susceptible versus drug-resistant strains, and ranged from 0.03-4 µg/mL for clinically relevant resistant strains.

Compounds of the present invention showed broad spectrum antimycobacterial activity against all mycobacteria. Compounds described in Example 2, 5, 45 exhibited MIC$_{90}$'s (concentration which inhibits 90% of strains) ranging from 0.12-1 µg/mL for M. abscessus, M. chelonae, and M. fortuitum.

Mechanism of action. The elucidation of the mechanism of action of the benzothiazole amide series was performed. Evidence was obtained that compounds from this series affect the transfer of mycolic acids to their cell envelope acceptors in both Mabs and Mtb, most likely through the inhibition of the trehalose monomycolate transporter, MmpL3. This conclusion is supported by the facts that: 1) the metabolic labeling with [$^{14}$C]acetate of Mabs ATCC19977 cultures either untreated or treated with cyclohexyl amides at 2 and 10 times their MICs results in a concentration-dependent inhibition of mycolic acid transfer to both arabinogalactan and trehalose dimycolates, a hallmark of MmpL3 inhibitors (FIG. 1); 2) the screening of an M. smegmatis library expressing 75 different mutated variants of the MmpL3 protein from Mtb yielded eleven mutants showing more than a 4-fold increase (three mutants with more than a 8-fold increase) in their resistance to benzothiazole cyclohexyl amide inhibitors; 3) spontaneous-resistant Mabs ATCC19977 mutants to compound 79 and 80, an isolated on 7H11-ADC agar containing 4×MIC concentrations of the inhibitors were found to harbor non-synonymous mutations in their mmpL3 gene (L551S, I306S, A309P). The involvement of these mutations in the resistance phenotype of the spontaneous-resistant mutants was confirmed by showing that their introduction in the isogenic background of Mabs ATCC19977 by recombineering was sufficient to confer greater than a 4-fold increase in resistance to benzothiazole amide compounds.

The inhibitory effect of early lead compound CRS400153 (compound 80) on MmpL3 activity did not result from the collapse of the proton motive force from which MmpL3 derives its energy, as verified by monitoring the effect of CRS400153 treatment on the membrane potential and electrochemical pH gradient of Mtb intact cells and inverted membrane vesicles (data not shown).

The further testing of 16 analogs from the same compound class, indicated that all of them displayed reduced activity against CRS400153-resistant mutants harboring mutations in the mmpL3 gene. This data suggests that compounds from the structural class of CRS400153 act on MmpL3 as their primary biochemical target. In contrast, 8 structurally diverse compounds from a different subseries remained active against the CRS400153-resistant mutants despite some of these non-cross-resistant compounds also inhibiting the transfer of mycolic acids to their cell envelope acceptors in Mabs. Thus these compounds served as negative controls.

In Vivo Efficacy.

Several compounds were screened in mouse PK and tolerability studies to evaluate various doses and routes of administration. Although highly tolerated, it became clear that the lipophilic nature of the compounds made oral routes of administration for efficacy more difficult. Instead, intrapulmonary delivery methods for treatment of lung infections such as NTM and Mtb were explored. CRS400226 (compound 45), an earlier lead compound, was synthesized in multi-gram quantities to support in vivo work and was further developed for this delivery pathway. Although essentially insoluble in water, we found CRS400226 was soluble in corn oil at concentrations up to 250 mg/mL. Initial attempts to formulate CRS400226 as a corn oil/saline emulsion (5%) afforded the opportunity to obtain proof-of-concept in vivo efficacy. Working with Dr. Gonzalez-Juarrero at CSU, a leading expert on intra-tracheal delivery, we assessed CRS400226 against Mabs #21 in a 28-day mouse model of chronic NTM lung infection. The study used granulocyte macrophage colony stimulated factor-knockout (GM-CSF KO) mice, which represent a clinically relevant model of human infection. Chronic *M. abscessus* spp. (NTM) respiratory infections are readily established in these mice with this specific immune deficiency and pathologic changes (De Groote, 2014). The Penn Century microsprayer was used for delivery of $5\times10^5$ to $1\times10^6$ bacteria to the lungs. Starting 10 days later, the test compound was dosed once daily over 4 weeks by intratracheal microspray administration as 5% corn oil/saline emulsion. The bacterial loads in the lungs were determined by plating serial dilutions of homogenates on 7H11 agar and enumeration of colonies after incubation at 37° C. CRS400226 demonstrated a statistically significant CFU reduction compared to the vehicle control at 25 mg/kg (FIG. 2A) and was very well tolerated out to 4 weeks of dosing (FIG. 2B).

It will be clear that the invention is well adapted to attain the ends and advantages mentioned as well as those inherent therein. While several presently preferred embodiments have been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims.

The entire disclosure and all publications cited herein are hereby incorporated by reference.

What is claimed is:

1. A compound of Formula (I):

Formula I 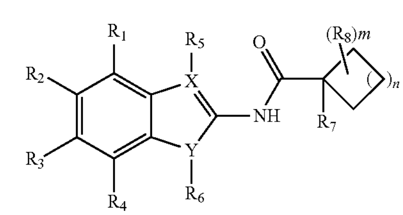 in which:

X is selected from C or N,

Y is selected from N, O or S, n=1-6

R1, R2, R3, R4 are independently selected from the group consisting of H, halogens, small alkyl (C1-C6), small alkyloxy (C1-C6), halogenated small alkyl (C1-C6), halogenated small alkyloxy (C1-C6), and carboxylates, when X is carbon, R5 is selected from the group consisting of H, alkyl, halogens, and cyano, when X is nitrogen, R5 is null, when Y is nitrogen, R6 is selected from the group consisting of H, alkyl, and substituted alkyl, when Y is O or S, R6 is null, R7 is selected from the group consisting of H, small alkyl (C1-C6), halogenated small alkyl (C1-C6), R7 can not be H when n<3, each R8 is independently selected from the group consisting of H, small alkyl (C1-C6), halogenated small alkyl (C1-C6), m is 1-6, R7 and R8 can link together to form rings when they are alkyl or halogenated alkyl with proviso that does not include: 4-propylcyclohexane-1-carbonyl, 1,2,2,3,3,4,4,5,5,6,6-undecafluorocyclohexane-1-carbonyl, 4-methylcyclohexane-1-carbonyl, 4-butylcyclohexane-1-carbonyl, cyclohexanecarbonyl, cyclopentanecarbonyl, cyclobutanecarbonyl, cycloheptanecarbonyl, 3-(trifluoromethyl)cyclohexane-1-carbonyl, 4,4-difluorocyclohexane-1-carbonyl, bicyclo[3.1.0]hexane-3-carbonyl, 1-methylcyclopentane-1-carbonyl, bicyclo[2.2.1]heptane-2-carbonyl, adamantane-1-carbonyl, 3-bromoadamantane-1-carbonyl, 3-chloroadamantane-1-carbonyl, 3,5-dimethyladamantane-1-carbonyl, 3-methyladamantane-1-carbonyl, 5,5,6-trifluoro-6-(trifluoromethyl)bicyclo[2.2.1]heptane-2-carbonyl, adamantane-2-carbonyl.

2. The compound of claim 1, wherein

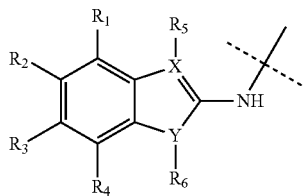

is: 5-trifluoromethyl-benzo[d]thiazol-2-amine; 6-isopropyl-benzo[d]thiazol-2-amine; 6-butyl-benzo[d]thiazol-2-amine, 6-dimethylamino-benzo[d]thiazol-2-amine, [1,3]dioxolo[4′,5′:4,5]benzo[1,2-d]thiazol-6-amine, 6-ethoxybenzo[d]thiazol-2-amine, 6-isopropoxybenzo[d]thiazol-2-amine, 5,7-difluorobenzo[d]thiazol-2-amine, 5,7-dichlorobenzo[d]thiazol-2-amine, 5,7-dimethylbenzo[d]thiazol-2-amine, 6-(methylthio)benzo[d]thiazol-2-amine, 6-(difluoromethoxy)benzo[d]thiazol-2-amine, 6-(trifluoromethoxy)benzo[d]thiazol-2-amine, 6-(tert-butyl)benzo[d]thiazol-2-amine, 7-fluorobenzo[d]thiazol-2-amine, 6-bromo-4-fluoro-benzo[d]thiazol-2-amine, 5-bromo-benzo[d]thiazol-2-amine, 5-chloro-benzo[d]thiazol-2-amine, ethyl 2-aminobenzo[d]thiazole-6-carboxylate, 6-bromo-benzo[d]thiazol-2-amine, 5-fluoro-benzo[d]thiazol-2-amine, 4-fluoro-benzo[d]thiazol-2-amine, 5,6-difluoro-benzo[d]thiazol-2-amine, 4,5,6-trifluoro-benzo[d]thiazol-2-amine, 4,6-dichloro-benzo[d]thiazol-2-amine, 6-methyl-benzo[d]thiazol-2-amine, 6-fluoro-benzo[d]thiazol-2-amine, benzo[d]thiazol-2-amine, 4-fluoro-benzo[d]thiazol-2-amine, 6-chloro-benzo[d]thiazol-2-amine, 6-methoxy-benzo[d]thiazol-2-amine, 6-trifluoromethyl-benzo[d]thiazol-2-amine, 4,6-difluoro-benzo[d]thiazol-2-amine, 4-trifluoromethyl-benzo[d]thiazol-2-amine, or 6-trifluoromethyl-benzo[d]thiazol-2-amine.

3. The compound of claim 1, wherein

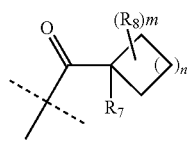

is: (1R,2R,4R)-2-methylbicyclo[2.2.1]hept-5-ene-2-carbonyl, (1R,2S,4R)-2-methylbicyclo[2.2.1]hept-5-ene-2-carbonyl, decahydronaphthalene-2-carbonyl, (1R,3S)-1,2,2,3-tetramethylcyclopentane-1-carbonyl, 3,3-difluoro-1-methylcyclopentane-1-carbonyl, 3,3-dimethylcyclopentane-1-carbonyl, 1-ethylcyclopentane-1-carbonyl, 3-methylcyclopentane-1-carbonyl, cyclopentanecarbonyl, 1-methylcycloheptane-1-carbonyl, 1,2-dimethylcyclopentane-1-carbonyl, 2-methylbicyclo[2.2.1]heptane-2-carbonyl, 1,3-dimethylcyclopentane-1-carbonyl, 1-isobutylcyclopentane-1-carbonyl, pivalyl, 2-methyl-7-oxabicyclo[2.2.1]heptane-2-carbonyl, 5-methylbicyclo[3.3.1]nonane-1-carbonyl, 3-methylbicyclo[3.1.0]hexane-3-carbonyl, 1-ethylcyclohexane-1-carbonyl, 1-methylcyclohexane-1-carbonyl, bicyclo[3.3.1]nonane-3-carbonyl, cyclohexanecarbonyl, cyclooctanecarbonyl, or 3,3,5-trimethylcyclohexane-1-carbonyl.

4. A compound selected from the group consisting of: N-(1-benzothiophen-2-yl)-5-methylbicyclo[3.3.1]nonane-1-carboxamide, N-(5,7-dichloro-1,3-benzothiazol-2-yl)-5-methylbicyclo[3.3.1]nonane-1-carboxamide, N-(5-bromo-1,3-benzothiazol-2-yl)-5-methylbicyclo[3.3.1]nonane-1-carboxamide, N-(5,7-difluoro-1,3-benzothiazol-2-yl)-5-methylbicyclo[3.3.1]nonane-1-carboxamide, 5-methyl-N-[6-(trifluoromethoxy)-1,3-benzothiazol-2-yl]bicyclo[3.3.1]nonane-1-carboxamide, 1-methyl-N-[6-(trifluoromethoxy)-1,3-benzothiazol-2-yl]cycloheptane-1-carboxamide, N-[6-(trifluoromethoxy)-1,3-benzothiazol-2-yl]adamantane-2-carboxamide, N-(5,7-dimethyl-1,3-benzothiazol-2-yl)-5-methylbicyclo[3.3.1]nonane-1-carboxamide, 5-methyl-N-(4,5,6-trifluoro-1,3-benzothiazol-2-yl)bicyclo[3.3.1]nonane-1-carboxamide, N-(4,6-difluoro-1,3-benzothiazol-2-yl)-5-methylbicyclo[3.3.1]nonane-1-carboxamide, N-(6-bromo-1,3-benzothiazol-2-yl)-5-methylbicyclo[3.3.1]nonane-1-carboxamide, N-(6-chloro-1,3-benzothiazol-2-yl)-5-methylbicyclo[3.3.1]nonane-1-carboxamide, N-[6-(difluoromethoxy)-1,3-benzothiazol-2-yl]-5-methylbicyclo[3.3.1]nonane-1-carboxamide, (3R,5S,7s)-N-[6-(trifluoromethoxy)-1,3-benzothiazol-2-yl]adamantane-1-carboxamide, N-[6-(trifluoromethoxy)-1,3-benzothiazol-2-yl]bicyclo[3.3.1]nonane-3-carboxamide, N-[6-(trifluoromethoxy)-1,3-benzothiazol-2-yl]-decahydronaphthalene-2-carboxamide, (1R,3S)-1,2,2,3-tetramethyl-N-[6-(trifluoromethoxy)-1,3-benzothiazol-2-yl]cyclopentane-1-carboxamide, N-(5,7-dichloro-1,3-benzothiazol-2-yl)-1-methylcycloheptane-1-carboxamide, N-(1-benzothiophen-2-yl)adamantane-2-carboxamide, N-(5,7-dichloro-1,3-benzothiazol-2-yl)adamantane-2-carboxamide, 5-methyl-N-[6-(trifluoromethyl)-1,3-benzothiazol-2-yl]bicyclo[3.3.1]nonane-1-carboxamide, 1,3-dimethyl-N-[6-(trifluoromethoxy)-1,3-benzothiazol-2-yl]cyclopentane-1-carboxamide, N-(5,7-dichloro-1,3-benzothiazol-2-yl)-1-methylcyclohexane-1-carboxamide, N-(5-bromo-1-benzothiophen-2-yl)-3,5-dimethyladamantane-1-carboxamide, 3,3,5-trimethyl-N-[5-(trifluoromethyl)-1,3-benzothiazol-2-yl]cyclohexane-1-carboxamide, N-(1-benzothiophen-2-yl)adamantane-1-carboxamide, 1-ethyl-N-[6-(trifluoromethoxy)-1,3-benzothiazol-2-yl]cyclohexane-1-carboxamide, 1-methyl-N-[6-(trifluoromethoxy)-1,3-benzothiazol-2-yl]cyclohexane-1-carboxamide, N-[6-(trifluoromethoxy)-1,3-benzothiazol-2-yl]tricyclo[3.3.1.0$^{3,7}$]nonane-3-carboxamide, (3R,5S,7s)-N-(4,5,6-trifluoro-1,3-benzothiazol-2-yl)adamantane-1-carboxamide, N-(5,7-difluoro-1,3-benzothiazol-2-yl)-3,5-dimethyladamantane-1-carboxamide, N-(5,7-difluoro-1,3-benzothiazol-2-yl)-3,3,5-trimethylcyclohexane-1-carboxamide, N-(4,6-difluoro-1,3-benzothiazol-2-yl)bicyclo[3.3.1]nonane-3-carboxamide, N-(5,7-dichloro-1,3-benzothiazol-2-yl)-3,5-dimethyladamantane-1-carboxamide, N-(5,7-dichloro-1,3-benzothiazol-2-yl)-3,3,5-trimethylcyclohexane-1-carboxamide, N-[6-(trifluoromethoxy)-1,3-benzothiazol-2-yl]cyclooctanecarboxamide, N-(5-chloro-1,3-benzothiazol-2-yl)-3,5-dimethyladamantane-1-carboxamide, N-(6-chloro-1,3-benzothiazol-2-yl)-3,5-dimethyladamantane-1-carboxamide, (1R,3R,7r)-3,5-dimethyl-N-[6-(trifluoromethyl)-1,3-benzothiazol-2-yl]adamantane-1-carboxamide, N-(1-benzothiophen-2-yl)bicyclo[3.3.1]nonane-3-carboxamide, N-(4,5,6-trifluoro-1,3-benzothiazol-2-yl)bicyclo[3.3.1]nonane-3-carboxamide, N-(1-benzothiophen-2-yl)-3,5-dimethyladamantane-1-carboxamide, N-(7-fluoro-1,3-benzothiazol-2-yl)-3,5-dimethyladamantane-1-carboxamide, N-(5,6-difluoro-1,3-benzothiazol-2-yl)-3,5-dimethyladamantane-1-carboxamide, 3,5-dimethyl-N-[6-(trifluoromethoxy)-1,3-benzothiazol-2-yl]adamantane-1-carboxamide, 3,3,5-trimethyl-N-[6-(trifluoromethoxy)-1,3-benzothiazol-2-yl]cyclohexane-1- carboxamide, N-(1-benzothiophen-2-yl)-3,3,5-trimethylcyclohexane-1-carboxamide, N-(5-bromo-1,3-benzothiazol-2-yl)-3,5-dimethyladamantane-1-carboxamide, N-(5,7-dichloro-1,3-benzothiazol-2-yl)-1-methylcyclopentane-1-carboxamide, (1R,2R,4R)-2-methyl-N-[6-(trifluoromethoxy)-1,3-benzothiazol-2-yl]bicyclo[2.2.1]hept-5-ene-2-carboxamide, 3,3-dimethyl-N-[6-(trifluoromethoxy)-1,3-benzothiazol-2-yl]cyclopentane-1-carboxamide, 1-methyl-N-[6-(trifluoromethyl)-1,3-benzothiazol-2-yl]cycloheptane-1-carboxamide, N-(5-bromo-1,3-benzothiazol-2-yl)-1-methylcycloheptane-1-carboxamide, N-(1-benzothiophen-2-yl)-1-methylcycloheptane-1-carboxamide, N-(6-bromo-1,3-benzothiazol-2-yl)adamantane-2-carboxamide, N-(6-chloro-1,3-benzothiazol-2-yl)adamantane-2-carboxamide, N-(5,7-difluoro-1,3-benzothiazol-2-yl)adamantane-2-carboxamide, N-(4,5,6-trifluoro-1,3-benzothiazol-2-yl)adamantane-2-carboxamide, N-[6-(difluoromethoxy)-1,3-benzothiazol-2-yl]adamantane-2-carboxamide, 1,2-dimethyl-N-[6-(trifluoromethoxy)-1,3-benzothiazol-2-yl]cyclopentane-1-carboxamide, 3,5-dimethyl-N-[5-(trifluoromethyl)-1,3-benzothiazol-2-yl]adamantane-1-carboxamide, N-(6-bromo-1,3-benzothiazol-2-yl)bicyclo[3.3.1]nonane-3-carboxamide, N-[6-(difluoromethoxy)-1,3-benzothiazol-2-yl]bicyclo[3.3.1]nonane-3-carboxamide, N-(6-chloro-1,3-benzothiazol-2-yl)bicyclo[3.3.1]nonane-3-carboxamide, N-(5,7-dimethyl-1,3-benzothiazol-2-yl)-3,3,5-trimethylcyclohexane-1-carboxamide, N-(5,7-dichloro-1,3-benzoxazol-2-yl)-3,5-dimethyladamantane-1-carboxamide, 3,5-dimethyl-N-{6-[(trifluoromethyl)sulfanyl]-1,3-benzothiazol-2-yl}adamantane-1-carboxamide, N-[6-(difluoromethoxy)-1,3-benzothiazol-2-yl]-3,5-dimethyladamantane-1-carboxamide, N-(6-bromo-4-fluoro-1,3-benzothiazol-2-yl)-3,5-dimethyladamantane-1-carboxamide, N-(5-fluoro-1,3-benzothiazol-2-yl)-3,5-dimethyladamantane-1-carboxamide, N-(4,6-difluoro-1,3-benzothiazol-2-yl)-3,5-dimethyladamantane-1-carboxamide, N-(7-fluoro-1,3-benzothiazol-2-yl)-3,3,5-trimethylcyclohexane-1-carboxamide, N-(6-bromo-1,3-benzothiazol-2-yl)-3,5-dimethyladamantane-1-carboxamide, N-(6-fluoro-1,3-benzothiazol-2-yl)-3,3,5-trimethylcyclohexane-1-carboxamide, N-(6-chloro-1,3-benzothiazol-2-yl)-3,3,5-trimethylcyclohexane-1-carboxamide, N-(6-bromo-1,3-benzothiazol-2-yl)-3,3,5-trimethylcyclohexane-1-carboxamide, 3,3,5-trimethyl-N-(4,5,6-trifluoro-1,3-benzothiazol-2-yl)cyclohexane-1-carboxamide, 3,5-dimethyl-N-[6-(trifluoromethyl)-1,3-benzothiazol-2-yl]adamantane-1-carboxamide, 3,3,5-trimethyl-N-[6-(trifluoromethyl)-1,3-benzothiazol-2-yl]cyclohexane-1-carboxamide, N-(4,6-difluoro-1,3-benzothiazol-2-yl)-3,3,5-trimethylcyclohexane-1-carboxamide, 3,3-difluoro-1-methyl-N-[6-(trifluoromethoxy)-1,3-benzothiazol-2-yl]cyclopentane-1-carboxamide, N-(4,6-difluoro-1,3-benzothiazol-2-yl)adamantane-2-carboxamide, N-(5,7-dimethyl-1,3-benzothiazol-2-yl)adamantane-2-carboxamide, 1-methyl-N-[6-(trifluoromethyl)-1,3-benzothiazol-2-yl]cyclohexane-1-carboxamide, 1-(2-methylpropyl)-N-[6-(trifluoromethoxy)-1,3-benzothiazol-2-yl]cyclopentane-1-carboxamide, N-(4,6-difluoro-1,3-benzothiazol-2-yl)adamantane-1-carboxamide, N-[6-(difluoromethoxy)-1,3-benzothiazol-2-yl]adamantane-1-carboxamide, N-(5,6-difluoro-1,3-benzoxazol-2-yl)-3,5-dimethyladamantane-1-carboxamide, N-(1-benzothiophen-2-yl)cyclooctanecarboxamide, N-(5,7-dimethyl-1,3-benzothiazol-2-yl)-3,5-dimethyladamantane-1-carboxamide, N-[6-(difluoromethoxy)-1,3-benzothiazol-2-yl]-3,3,5-trimethylcyclohexane-1-carboxamide, N-(6-bromo-4-fluoro-1,3-benzothiazol-2-yl)-3,3,5-trimethylcyclohexane-1-carboxamide, N-(5-fluoro-1,3-benzothiazol-2-yl)-3,3,5-trimethylcyclohexane-1-carboxamide, N-(1,3-benzothiazol-2-yl)-3,5-dimethyladamantane-1-carboxamide, N-(4-chloro-1,3-benzothiazol-2-yl)-3,5-dimethyladamantane-1-carboxamide, N-(6-methoxy-1,3-benzothiazol-2-yl)-3,3,5-trimethylcyclohexane-1-carboxamide, N-(4,6-dichloro-1,3-benzothiazol-2-yl)-3,5-dimethyladamantane-1-carboxamide, 3,5-dimethyl-N-(6-methyl-1,3-benzothiazol-2-yl)adamantane-1-carboxamide, 3,5-dimethyl-N-[6-(trifluoromethyl)-1,3-benzothiazol-2-yl]cyclohexane-1-carboxamide, ethyl 2-(3,5-dimethyladamantane-1-amido)-1,3-benzothiazole-6-carboxylate, 1-ethyl-N-[6-(trifluoromethoxy)-1,3-benzothiazol-2-yl]cyclopentane-1-carboxamide, 3-methyl-N-[6-(trifluoromethoxy)-1,3-benzothiazol-2-yl]cyclopentane-1-carboxamide, 1-methyl-N-(4,5,6-trifluoro-1,3-benzothiazol-2-yl)cycloheptane-1-carboxamide, 2-methyl-N-[6-(trifluoromethoxy)-1,3-benzothiazol-2-yl]bicyclo[2.2.1]heptane-2-carboxamide, N-(1-benzothiophen-2-yl)-1-methylcyclohexane-1-carboxamide, N-(6-bromo-5,7-dimethyl-1,3-benzothiazol-2-yl)-1-methylcyclohexane-1-carboxamide, N-(6-chloro-1,3-benzothiazol-2-yl)adamantane-1-carboxamide, N-[6-(difluoromethoxy)-1,3-benzothiazol-2-yl]cyclooctanecarboxamide, N-(4,6-difluoro-1,3-benzothiazol-2-yl)cyclooctanecarboxamide, N-(6-chloro-1,3-benzothiazol-2-yl)cyclooctanecarboxamide, N-(6-ethoxy-1,3-benzothiazol-2-yl)-3,5-dimethyladamantane-1-carboxamide, N-(5,6-dichloro-1,3-benzoxazol-2-yl)-3,5-dimethyladamantane-1-carboxamide, N-(5,6-dichloro-1,3-benzoxazol-2-yl)-3,3,5-trimethylcyclohexane-1-carboxamide, N-(5-chloro-1,3-benzoxazol-2-yl)-3,3,5-trimethylcyclohexane-1-carboxamide, N-(6-bromo-1,3-benzoxazol-2-yl)-3,5-dimethyladamantane-1-carboxamide, N-(4,5,6-trifluoro-1,3-benzothiazol-2-yl)cyclooctanecarboxamide, N-(6-chloro-1,3-benzoxazol-2-yl)-3,5-dimethyladamantane-1-carboxamide, N-(6-chloro-1,3-benzoxazol-2-yl)-3,3,5-trimethylcyclohexane-1-carboxamide, N-(5,6-difluoro-1H-1,3-benzodiazol-2-yl)-3,5-dimethyladamantane-1-carboxamide, N-(6-fluoro-1H-1,3-benzodiazol-2-yl)-3,5-dimethyladamantane-1-carboxamide, N-(4-fluoro-1,3-benzothiazol-2-yl)-3,3,5-trimethylcyclohexane-1-carboxamide, N-(4-fluoro-1,3-benzothiazol-2-yl)-3,5-dimethyladamantane-1-carboxamide, N-(6-fluoro-1,3-benzothiazol-2-yl)-3,5-dimethyladamantane-1-carboxamide, N-(6-methoxy-1,3-benzothiazol-2-yl)-3,5-dimethyladamantane-1-carboxamide, N-(1,3-benzothiazol-2-yl)-3,3,5-trimethylcyclohexane-1-carboxamide, 3-(trifluoromethyl)-N-[6-(trifluoromethyl)-1,3-benzothiazol-2-yl]cyclohexane-1-carboxamide, 3-methyl-N-[6-(trifluoromethyl)-1,3-benzothiazol-2-yl]cyclohexane-1-carboxamide, 1-methyl-N-[6-(trifluoromethyl)-1,3-benzothiazol-2-yl]cyclopentane-1-carboxamide, (1R,2S,4R)-2-methyl-N-[6-(trifluoromethoxy)-1,3-benzothiazol-2-yl]bicyclo[2.2.1]hept-5-ene-2-carboxamide, N-[6-(trifluoromethoxy)-1,3-benzothiazol-2-yl]cyclopentanecarboxamide, N-(1,3-benzoxazol-2-yl)adamantane-2-carboxamide, 5-methyl-N-[6-(trifluoromethyl)-1,3-benzoxazol-2-yl]bicyclo[3.3.1]nonane-1-carboxamide, N-(5,7-difluoro-1,3-benzothiazol-2-yl)-1-methylcyclohexane-1-carboxamide, N-(6-bromo-1,3-benzothiazol-2-yl)-1-methylcyclohexane-1-carboxamide, N-(6-chloro-1,3-benzothiazol-2-yl)-1-methylcyclohexane-1-carboxamide, 1-methyl-N-[6-(trifluoromethoxy)-1,3-benzothiazol-2-yl]cyclopentane-1-carboxamide, 3-methyl-N-[6-(trifluoromethoxy)-1,3-benzothiazol-2-yl]bicyclo[3.1.0]hexane-3-carboxamide, N-(6-ethoxy-1,3-benzothiazol-2-yl)

bicyclo[3.3.1]nonane-3-carboxamide, N-(4,6-difluoro-1,3-benzothiazol-2-yl)cycloheptanecarboxamide, N-(5-chloro-1,3-benzoxazol-2-yl)-3,5-dimethyladamantane-1-carboxamide, N-(4,5,6-trifluoro-1,3-benzothiazol-2-yl)cycloheptanecarboxamide, N-(5,7-dichloro-1,3-benzoxazol-2-yl)-3,3,5-trimethylcyclohexane-1-carboxamide, N-(5,7-dimethyl-1,3-benzoxazol-2-yl)-3,3,5-trimethylcyclohexane-1-carboxamide, N-(4-fluoro-1,3-benzoxazol-2-yl)-3,5-dimethyladamantane-1-carboxamide, N-(6-methoxy-1,3-benzoxazol-2-yl)-3,5-dimethyladamantane-1-carboxamide, N-(1H-1,3-benzodiazol-2-yl)-3,5-dimethyladamantane-1-carboxamide, N-(1,3-benzoxazol-2-yl)-3,5-dimethyladamantane-1-carboxamide, N-[6-(trifluoromethyl)-1,3-benzothiazol-2-yl]spiro[2.5]octane-5-carboxamide, 1-(3-methylcyclohexyl)-3-[6-(trifluoromethyl)-1,3-benzothiazol-2-yl]urea, 3,5-dimethyl-N-[6-(trifluoromethyl)-1,3-benzoxazol-2-yl]adamantane-1-carboxamide, N-(5,6-dichloro-1H-1,3-benzodiazol-2-yl)-3,3,5-trimethylcyclohexane-1-carboxamide, 3-methyl-N-[6-(trifluoromethyl)-1,3-benzothiazol-2-yl]cyclopentane-1-carboxamide, N-(5-bromo-1,3-benzothiazol-2-yl)-1-methylcyclopentane-1-carboxamide, 1-methyl-N-(4,5,6-trifluoro-1,3-benzothiazol-2-yl)cyclohexane-1-carboxamide, N-(1,3-benzoxazol-2-yl)adamantane-1-carboxamide, N-[6-(difluoromethoxy)-1,3-benzothiazol-2-yl]cyclohexanecarboxamide, N-(4,6-difluoro-1,3-benzothiazol-2-yl)cyclohexanecarboxamide, N-(6-bromo-1,3-benzoxazol-2-yl)-3,3,5-trimethylcyclohexane-1-carboxamide, N-(1,3-benzoxazol-2-yl)bicyclo[3.3.1]nonane-3-carboxamide, N-(1-benzothiophen-2-yl)cycloheptanecarboxamide, N-(5,7-dimethyl-1,3-benzoxazol-2-yl)-3,5-dimethyladamantane-1-carboxamide, N-(6-methoxy-1,3-benzoxazol-2-yl)-3,3,5-trimethylcyclohexane-1-carboxamide, 3,3,5-trimethyl-N-[6-(trifluoromethyl)-1,3-benzoxazol-2-yl]cyclohexane-1-carboxamide, N-(5,6-dichloro-1H-1,3-benzodiazol-2-yl)-3,5-dimethyladamantane-1-carboxamide, N-(1,3-benzoxazol-2-yl)-3,3,5-trimethylcyclohexane-1-carboxamide, N-(1,3-benzothiazol-2-yl)-2-methylcyclohexane-1-carboxamide, N-(4-chloro-1,3-benzothiazol-2-yl)-3-methylcyclohexane-1-carboxamide, N-(6-chloro-1,3-benzothiazol-2-yl)-3-methylcyclohexane-1-carboxamide, N-(4,6-difluoro-1,3-benzothiazol-2-yl)-3-methylcyclohexane-1-carboxamide, N-(6-fluoro-1,3-benzothiazol-2-yl)-3-methylcyclohexane-1-carboxamide, N-(4,6-difluoro-1,3-benzothiazol-2-yl)-1-methylcyclohexane-1-carboxamide, N-[6-(difluoromethoxy)-1,3-benzothiazol-2-yl]-1-methylcyclohexane-1-carboxamide, 2,2-dimethyl-N-[6-(trifluoromethoxy)-1,3-benzothiazol-2-yl]propanamide, N-(7-hydroxy-1,3-benzothiazol-2-yl)-3,3,5-trimethylcyclohexane-1-carboxamide, N-(5,6-difluoro-1,3-benzoxazol-2-yl)-3,3,5-trimethylcyclohexane-1-carboxamide, N-(1-benzothiophen-2-yl)cyclohexanecarboxamide, 3,3,5-trimethyl-N-{6-[(trifluoromethyl)sulfanyl]-1,3-benzothiazol-2-yl}cyclohexane-1-carboxamide, N-(6-fluoro-1H-1,3-benzodiazol-2-yl)-3,3,5-trimethylcyclohexane-1-carboxamide, N-(4-chloro-1,3-benzothiazol-2-yl)-3,3,5-trimethylcyclohexane-1-carboxamide, 3-methyl-N-(4-methyl-1,3-benzothiazol-2-yl)cyclohexane-1-carboxamide, N-(6-methoxy-1,3-benzothiazol-2-yl)-3-methylcyclohexane-1-carboxamide, N-(1,3-benzothiazol-2-yl)-3-methylcyclohexane-1-carboxamide, N-(4-methyl-1,3-benzothiazol-2-yl)bicyclo[2.2.1]heptane-2-carboxamide, N-(5,7-dichloro-1,3-benzoxazol-2-yl)-5-methylbicyclo[3.3.1]nonane-1-carboxamide, 2-methyl-N-[6-(trifluoromethoxy)-1,3-benzothiazol-2-yl]-7-oxabicyclo[2.2.1]heptane-2-carboxamide, N-[6-(dimethylamino)-1,3-benzothiazol-2-yl]-3,3,5-trimethylcyclohexane-1-carboxamide, N-(1,3-benzoxazol-2-yl)cyclooctanecarboxamide, N-[6-(trifluoromethoxy)-1,3-benzothiazol-2-yl]cyclohexanecarboxamide, N-(4,6-difluoro-1,3-benzoxazol-2-yl)-3,3,5-trimethylcyclohexane-1-carboxamide, N-(5-bromo-1,3-benzothiazol-2-yl)-3,3,5-trimethylcyclohexane-1-carboxamide, N-(6-chloro-1,3-benzothiazol-2-yl)-3-methoxycyclohexane-1-carboxamide, and N-[6-(trifluoromethyl)-1,3-benzothiazol-2-yl]spiro[2.5]octane-6-carboxamide.

5. A pharmaceutical composition comprising a therapeutically effective amount of a compound according to claim 1 or a pharmaceutically acceptable salt of a compound of claim 1.

6. A pharmaceutical composition comprising a therapeutically effective amount of a compound according to claim 4 or a pharmaceutically acceptable salt of a compound of claim 4.

7. A method of treating a patient diagnosed with a mycobacterial infection, said method comprising administering a therapeutically effective amount of a compound of claim 1 or a pharmaceutically acceptable salt or solvate thereof to the diagnosed patient.

8. A method of protecting a patient from a mycobacterial infection, said method comprising administering a therapeutically effective amount of a compound of claim 1 or a pharmaceutically acceptable salt or solvate thereof to the patient in the absence of a diagnosed mycobacterial infection.

* * * * *